(12) United States Patent
Gross et al.

(10) Patent No.: US 9,592,136 B2
(45) Date of Patent: *Mar. 14, 2017

(54) DEVICES AND METHODS FOR CONTROL OF BLOOD PRESSURE

(71) Applicant: Vascular Dynamics, Inc., Mountain View, CA (US)

(72) Inventors: Yossi Gross, Moshav Mazor (IL); Ori Weisberg, Shdema (IL); Itzik Avneri, Tel Aviv (IL)

(73) Assignee: Vascular Dynamics, Inc., Mountain View, CA (US)

( * ) Notice: Subject to any disclaimer, the term of this patent is extended or adjusted under 35 U.S.C. 154(b) by 243 days.

This patent is subject to a terminal disclaimer.

(21) Appl. No.: 14/092,433

(22) Filed: Nov. 27, 2013

(65) Prior Publication Data

US 2014/0135902 A1    May 15, 2014

Related U.S. Application Data

(63) Continuation-in-part of application No. 12/774,254, filed on May 5, 2010, now abandoned, which is a
(Continued)

(51) Int. Cl.
*A61F 2/82* (2013.01)
*A61B 5/042* (2006.01)
(Continued)

(52) U.S. Cl.
CPC ............ *A61F 2/82* (2013.01); *A61B 5/042* (2013.01); *A61B 5/6882* (2013.01);
(Continued)

(58) Field of Classification Search
CPC .................................................. A61F 2002/068
See application file for complete search history.

(56) References Cited

U.S. PATENT DOCUMENTS

| 3,650,277 A | 3/1972 | Sjostrand et al. |
| 4,201,219 A | 5/1980 | Bozal |

(Continued)

FOREIGN PATENT DOCUMENTS

| EP | 0791341 A1 | 8/1997 |
| EP | 1127557 A1 | 8/2001 |

(Continued)

OTHER PUBLICATIONS

Office action dated Jan. 2, 2015 for U.S. Appl. No. 13/455,005.
(Continued)

*Primary Examiner* — Christian Sevilla
*Assistant Examiner* — Megan Wolf
(74) *Attorney, Agent, or Firm* — Wilson, Sonsini, Goodrich & Rosati

(57) ABSTRACT

Apparatus and methods are described, including identifying a subject as suffering from hypertension. In response to the identifying (a) a radius of curvature of a first set of at least three regions of an arterial wall of the subject is increased at a given longitudinal location, while (b) allowing the first set of regions of the arterial wall to pulsate. A device is implanted inside the artery at the longitudinal location such that the device applies pressure to the arterial wall at a second set of at least three regions of the artery, but does not contact the first set of regions, the first set of regions and the second set of regions alternating with each other. Other embodiments are also described.

7 Claims, 8 Drawing Sheets

Related U.S. Application Data continuation-in-part of application No. 12/602,787, filed as application No. PCT/IL2009/000932 on Sep. 29, 2009, now Pat. No. 9,125,567, application No. 14/092,433, which is a continuation-in-part of application No. 11/881,256, filed on Jul. 25, 2007, now Pat. No. 8,923,972, which is a continuation-in-part of application No. PCT/IL2006/000856, filed on Jul. 25, 2006.

(60) Provisional application No. 61/194,339, filed on Sep. 26, 2008, provisional application No. 60/702,491, filed on Jul. 25, 2005, provisional application No. 60/721,728, filed on Sep. 28, 2005.

(51) Int. Cl.
 *A61F 2/06* (2013.01)
 *A61B 5/00* (2006.01)

(52) U.S. Cl.
 CPC . *A61F 2002/068* (2013.01); *A61F 2230/0017* (2013.01); *A61F 2230/0019* (2013.01); *A61F 2230/0023* (2013.01)

(56) References Cited

U.S. PATENT DOCUMENTS

| | | | |
|---|---|---|---|
| 4,791,931 A | 12/1988 | Slate | |
| 4,830,003 A | 5/1989 | Wolff | |
| 4,887,613 A | 12/1989 | Farr et al. | |
| 4,938,766 A | 7/1990 | Jarvik | |
| 5,403,341 A | 4/1995 | Solar | |
| 5,437,285 A | 8/1995 | Verrier et al. | |
| 5,458,626 A | 10/1995 | Krause | |
| 5,630,829 A | 5/1997 | Lauterjung | |
| 5,669,924 A | 9/1997 | Shaknovich | |
| 5,707,400 A | 1/1998 | Terry, Jr. et al. | |
| 5,727,558 A | 3/1998 | Hakki et al. | |
| 5,792,155 A | 8/1998 | Van Cleef | |
| 6,013,085 A | 1/2000 | Howard | |
| 6,086,527 A | 7/2000 | Talpade | |
| 6,093,203 A | 7/2000 | Uflacker | |
| 6,306,141 B1 | 10/2001 | Jervis | |
| 6,322,553 B1 | 11/2001 | Vito | |
| 6,375,666 B1 | 4/2002 | Mische | |
| 6,413,273 B1 | 7/2002 | Baum | |
| 6,442,424 B1 | 8/2002 | Ben-Haim et al. | |
| 6,520,987 B1 | 2/2003 | Plante | |
| 6,522,926 B1 | 2/2003 | Kieval et al. | |
| 6,554,856 B1 | 4/2003 | Doorly et al. | |
| 6,575,994 B1 | 6/2003 | Marin et al. | |
| 6,616,624 B1 | 9/2003 | Kieval | |
| 6,641,605 B1 | 11/2003 | Stergiopulos | |
| 6,666,883 B1 | 12/2003 | Seguin et al. | |
| 6,669,686 B1 | 12/2003 | Singh | |
| 6,681,136 B2 | 1/2004 | Schuler et al. | |
| 6,764,498 B2 | 7/2004 | Mische | |
| 6,850,801 B2 | 2/2005 | Kieval et al. | |
| 6,899,669 B2 | 5/2005 | Vito et al. | |
| 6,957,106 B2 | 10/2005 | Schuler et al. | |
| 6,972,031 B1 | 12/2005 | Braginsky et al. | |
| 6,974,445 B2 | 12/2005 | Stergiopulos | |
| 6,985,774 B2 | 1/2006 | Kieval et al. | |
| 7,008,446 B1 | 3/2006 | Amis et al. | |
| 7,044,981 B2 | 5/2006 | Liu et al. | |
| 7,060,080 B2 | 6/2006 | Bachmann | |
| 7,094,254 B2 | 8/2006 | Stergiopulos | |
| 7,128,750 B1 | 10/2006 | Stergiopulos | |
| 7,158,832 B2 | 1/2007 | Kieval et al. | |
| 7,159,593 B2 | 1/2007 | McCarthy et al. | |
| 7,194,313 B2 | 3/2007 | Libbus | |
| 7,201,772 B2 | 4/2007 | Schwammenthal | |
| 7,218,964 B2 | 5/2007 | Hill et al. | |
| 7,238,191 B2 | 7/2007 | Bachmann | |
| 7,270,675 B2 | 9/2007 | Chun | |
| 7,300,449 B2 | 11/2007 | Mische | |
| 7,331,987 B1 | 2/2008 | Cox | |
| 7,373,204 B2 | 5/2008 | Gelfand et al. | |
| 7,381,222 B2 | 6/2008 | Pflueger et al. | |
| 7,389,149 B2 | 6/2008 | Rossing et al. | |
| 7,395,119 B2 | 7/2008 | Hagen | |
| 7,491,229 B2 | 2/2009 | Eder | |
| 7,530,995 B2 | 5/2009 | Quijano et al. | |
| 7,625,399 B2 | 12/2009 | Case et al. | |
| 7,625,400 B2 | 12/2009 | Bowe | |
| 7,628,803 B2 | 12/2009 | Pavcnik et al. | |
| 7,637,937 B2 | 12/2009 | Case et al. | |
| 7,647,931 B2 | 1/2010 | Pflueger et al. | |
| 8,361,140 B2 | 1/2013 | Meyer et al. | |
| 8,923,972 B2 | 12/2014 | Gross | |
| 9,125,732 B2 * | 9/2015 | Gross | A61F 2/06 |
| 2001/0003801 A1 | 6/2001 | Strecker | |
| 2002/0035392 A1 | 3/2002 | Wilson | |
| 2002/0052646 A1 | 5/2002 | Fischell et al. | |
| 2002/0173838 A1 | 11/2002 | Frazier | |
| 2002/0183830 A1 | 12/2002 | Su et al. | |
| 2003/0060585 A1 | 3/2003 | Radhakrishna et al. | |
| 2003/0060858 A1 | 3/2003 | Kieval et al. | |
| 2003/0199806 A1 | 10/2003 | Kieval | |
| 2004/0010303 A1 | 1/2004 | Bolea et al. | |
| 2004/0019364 A1 | 1/2004 | Kieval et al. | |
| 2004/0106976 A1 | 6/2004 | Bailey et al. | |
| 2004/0111006 A1 | 6/2004 | Alferness et al. | |
| 2004/0149294 A1 | 8/2004 | Gianchandani et al. | |
| 2004/0167635 A1 | 8/2004 | Yachia et al. | |
| 2004/0193092 A1 | 9/2004 | Deal | |
| 2004/0249442 A1 | 12/2004 | Fleming et al. | |
| 2004/0254616 A1 | 12/2004 | Rossing et al. | |
| 2005/0027346 A1 | 2/2005 | Arbusz et al. | |
| 2005/0033407 A1 | 2/2005 | Weber | |
| 2005/0090894 A1 | 4/2005 | Pazienza et al. | |
| 2005/0096710 A1 | 5/2005 | Kieval | |
| 2005/0143765 A1 | 6/2005 | Bachmann et al. | |
| 2005/0143766 A1 | 6/2005 | Bachmann et al. | |
| 2005/0143785 A1 | 6/2005 | Libbus | |
| 2005/0149128 A1 | 7/2005 | Heil, Jr. et al. | |
| 2005/0149131 A1 | 7/2005 | Libbus et al. | |
| 2005/0149143 A1 | 7/2005 | Libbus et al. | |
| 2005/0154418 A1 | 7/2005 | Kieval et al. | |
| 2005/0203610 A1 | 9/2005 | Tzeng | |
| 2005/0232965 A1 | 10/2005 | Falotico | |
| 2005/0251212 A1 | 11/2005 | Kieval et al. | |
| 2005/0261257 A1 | 11/2005 | Vermeer | |
| 2006/0004417 A1 | 1/2006 | Rossing et al. | |
| 2006/0004420 A1 | 1/2006 | Rossing et al. | |
| 2006/0004430 A1 | 1/2006 | Rossing et al. | |
| 2006/0074453 A1 | 4/2006 | Kieval et al. | |
| 2006/0089678 A1 | 4/2006 | Shalev | |
| 2006/0111626 A1 | 5/2006 | Rossing et al. | |
| 2006/0217588 A1 | 9/2006 | Gross et al. | |
| 2006/0241334 A1 | 10/2006 | Dubi et al. | |
| 2006/0253193 A1 | 11/2006 | Lichtenstein et al. | |
| 2006/0265038 A1 | 11/2006 | Hagen et al. | |
| 2006/0276852 A1 | 12/2006 | Demarais et al. | |
| 2006/0293712 A1 | 12/2006 | Kieval et al. | |
| 2007/0021790 A1 | 1/2007 | Kieval et al. | |
| 2007/0021792 A1 | 1/2007 | Kieval et al. | |
| 2007/0021794 A1 | 1/2007 | Kieval et al. | |
| 2007/0021796 A1 | 1/2007 | Kieval et al. | |
| 2007/0021797 A1 | 1/2007 | Kieval et al. | |
| 2007/0021798 A1 | 1/2007 | Kieval et al. | |
| 2007/0021799 A1 | 1/2007 | Kieval et al. | |
| 2007/0038255 A1 | 2/2007 | Kieval et al. | |
| 2007/0038259 A1 | 2/2007 | Kieval et al. | |
| 2007/0038260 A1 | 2/2007 | Kieval et al. | |
| 2007/0038261 A1 | 2/2007 | Kieval et al. | |
| 2007/0038262 A1 | 2/2007 | Kieval et al. | |
| 2007/0049989 A1 | 3/2007 | Rossing et al. | |
| 2007/0055296 A1 | 3/2007 | Stergiopulos | |
| 2007/0060972 A1 | 3/2007 | Kieval et al. | |
| 2007/0100433 A1 | 5/2007 | Limon | |
| 2007/0106340 A1 | 5/2007 | Bolea et al. | |
| 2007/0142879 A1 | 6/2007 | Greenberg et al. | |

(56) References Cited

U.S. PATENT DOCUMENTS

| | | |
|---|---|---|
| 2007/0156167 A1 | 7/2007 | Connors et al. |
| 2007/0156198 A1 | 7/2007 | Rossing et al. |
| 2007/0156201 A1 | 7/2007 | Rossing |
| 2007/0167984 A1 | 7/2007 | Kieval et al. |
| 2007/0179519 A1 | 8/2007 | Huisun |
| 2007/0179599 A1 | 8/2007 | Brodbeck et al. |
| 2007/0185542 A1 | 8/2007 | Bolea et al. |
| 2007/0185543 A1 | 8/2007 | Rossing et al. |
| 2007/0187255 A1 | 8/2007 | Ogasawara et al. |
| 2007/0198082 A1 | 8/2007 | Kapadia et al. |
| 2007/0250085 A1 | 10/2007 | Bachmann et al. |
| 2007/0276442 A1 | 11/2007 | Hagen et al. |
| 2007/0276459 A1 | 11/2007 | Rossing et al. |
| 2007/0282385 A1 | 12/2007 | Rossing et al. |
| 2007/0287879 A1 | 12/2007 | Gelbart et al. |
| 2008/0004673 A1 | 1/2008 | Rossing et al. |
| 2008/0009916 A1 | 1/2008 | Rossing et al. |
| 2008/0009917 A1 | 1/2008 | Rossing et al. |
| 2008/0027469 A1 | 1/2008 | Bachmann |
| 2008/0033501 A1 | 2/2008 | Gross |
| 2008/0046054 A1 | 2/2008 | Hjelle et al. |
| 2008/0046072 A1 | 2/2008 | Laborde et al. |
| 2008/0051767 A1 | 2/2008 | Rossing et al. |
| 2008/0071135 A1 | 3/2008 | Shaknovich |
| 2008/0082137 A1 | 4/2008 | Kieval et al. |
| 2008/0097540 A1 | 4/2008 | Bolea et al. |
| 2008/0114439 A1 | 5/2008 | Ramaiah |
| 2008/0132966 A1 | 6/2008 | Levin et al. |
| 2008/0140167 A1 | 6/2008 | Hagen |
| 2008/0154349 A1 | 6/2008 | Rossing et al. |
| 2008/0161865 A1 | 7/2008 | Hagen |
| 2008/0161887 A1 | 7/2008 | Hagen |
| 2008/0167690 A1 | 7/2008 | Cody et al. |
| 2008/0167693 A1 | 7/2008 | Kieval et al. |
| 2008/0167694 A1 | 7/2008 | Bolea et al. |
| 2008/0167696 A1 | 7/2008 | Cates et al. |
| 2008/0167699 A1 | 7/2008 | Kieval et al. |
| 2008/0171923 A1 | 7/2008 | Bolea et al. |
| 2008/0172101 A1 | 7/2008 | Bolea et al. |
| 2008/0172104 A1 | 7/2008 | Kieval et al. |
| 2008/0177131 A1 | 7/2008 | Dancu |
| 2008/0181927 A1 | 7/2008 | Zhao |
| 2008/0194905 A1 | 8/2008 | Walsh |
| 2008/0195190 A1 | 8/2008 | Bland et al. |
| 2008/0275539 A1 | 11/2008 | Williams et al. |
| 2008/0319504 A1 | 12/2008 | Loushin |
| 2009/0216313 A1 | 8/2009 | Straubinger et al. |
| 2009/0248138 A1 | 10/2009 | Golesworthy et al. |
| 2009/0248141 A1 | 10/2009 | Shandas et al. |
| 2009/0264914 A1 | 10/2009 | Riina |
| 2009/0292348 A1 | 11/2009 | Berez et al. |
| 2009/0306756 A1 | 12/2009 | Cho |
| 2010/0211131 A1 | 8/2010 | Williams |
| 2011/0077729 A1 | 3/2011 | Gross |
| 2011/0178416 A1 | 7/2011 | Gross |
| 2011/0213408 A1 | 9/2011 | Gross |
| 2011/0230953 A1 | 9/2011 | Gross |
| 2011/0230957 A1 | 9/2011 | Bonsignore et al. |
| 2013/0172981 A1 | 7/2013 | Gross et al. |
| 2016/0058989 A1 | 3/2016 | Gross et al. |

FOREIGN PATENT DOCUMENTS

| | | |
|---|---|---|
| EP | 1153580 A1 | 11/2001 |
| EP | 1234554 A1 | 8/2002 |
| EP | 1343112 A1 | 9/2003 |
| EP | 1153581 B1 | 7/2004 |
| EP | 1200152 B1 | 9/2004 |
| EP | 1483730 A1 | 12/2004 |
| WO | WO 01/05463 A1 | 1/2001 |
| WO | WO 01/85063 A1 | 11/2001 |
| WO | WO 02/26314 A1 | 4/2002 |
| WO | WO 03/076008 A1 | 9/2003 |
| WO | WO 03/077191 A1 | 9/2003 |
| WO | WO 03/082080 A2 | 10/2003 |
| WO | WO 03/082403 A2 | 10/2003 |
| WO | WO 03/082403 A3 | 1/2004 |
| WO | WO 03/082080 A3 | 2/2004 |
| WO | WO 2004/073484 A2 | 9/2004 |
| WO | WO 2004/073484 A3 | 12/2004 |
| WO | WO 2005/021063 A2 | 3/2005 |
| WO | WO 2005/065771 A1 | 7/2005 |
| WO | WO 2005/084389 A2 | 9/2005 |
| WO | WO 2005/097256 A2 | 10/2005 |
| WO | WO 2005/021063 A3 | 2/2006 |
| WO | WO 2006/012033 A2 | 2/2006 |
| WO | WO 2006/012050 A2 | 2/2006 |
| WO | WO 2006/032902 A1 | 3/2006 |
| WO | WO 2006/040647 A1 | 4/2006 |
| WO | WO 2006/041664 A2 | 4/2006 |
| WO | WO 2006/042280 A2 | 4/2006 |
| WO | WO 2006/012033 A3 | 10/2006 |
| WO | WO 2005/084389 A3 | 11/2006 |
| WO | WO 2005/097256 A3 | 11/2006 |
| WO | WO 2006/012050 A3 | 11/2006 |
| WO | WO 2006/125163 A2 | 11/2006 |
| WO | WO 2007/013065 A2 | 2/2007 |
| WO | WO 2006/125163 A3 | 4/2007 |
| WO | WO 2007/047152 A2 | 4/2007 |
| WO | WO 2007/013065 A3 | 5/2007 |
| WO | WO 2007/080595 A2 | 7/2007 |
| WO | WO 2007/114860 A2 | 10/2007 |
| WO | WO 2007/118090 A2 | 10/2007 |
| WO | WO 2007/047152 A3 | 11/2007 |
| WO | WO 2007/136850 A2 | 11/2007 |
| WO | WO 2007/136851 A2 | 11/2007 |
| WO | WO 2008/039982 A2 | 4/2008 |
| WO | WO 2008/083120 A2 | 7/2008 |
| WO | WO 2008/083235 A3 | 7/2008 |
| WO | WO 2007/136850 A3 | 8/2008 |
| WO | WO 2008/039982 A3 | 8/2008 |
| WO | WO 2008/083120 A3 | 8/2008 |
| WO | WO 2008/083235 A3 | 9/2008 |
| WO | WO 2007/118090 A3 | 11/2008 |
| WO | WO 2007/136851 A3 | 11/2008 |
| WO | WO 2009/018394 A1 | 2/2009 |
| WO | WO 2006/041664 A3 | 4/2009 |
| WO | WO 2007/080595 A3 | 4/2009 |
| WO | WO 2007/114860 A3 | 4/2009 |
| WO | WO 2010/035271 A1 | 4/2010 |
| WO | WO 2011/089601 A1 | 7/2011 |

OTHER PUBLICATIONS

Office action dated Dec. 4, 2014 for U.S. Appl. No. 13/030,384.
U.S. Appl. No. 14/560,194, filed Dec. 4, 2014, Gross.
U.S. Appl. No. 60/702,491, filed Jul. 25, 2005, Gross.
U.S. Appl. No. 60/721,728, filed Sep. 28, 2005, Gross.
Davos. The effect of baroreceptor activity on cardiovascular regulation. Hellenic J. cardiol. 2002; 43:145-155.
European search report and opinion dated Dec. 14, 2012 for EP Application No. 06766171.
International search report and written opinion dated Jan. 24, 2007 for PCT/IL2006/000856.
Notice of Allowance dated Nov. 20, 2014 for U.S. Appl. No. 11/881,256.
Office action dated Jan. 14, 2013 for U.S. Appl. No. 11/881,256.
Office action dated May 24, 2012 for U.S. Appl. No. 11/881,256.
Office action dated Jun. 23, 2014 for U.S. Appl. No. 11/881,256.
Office action dated Oct. 21, 2014 for U.S. Appl. No. 13/116,370.
Office action dated Nov. 5, 2014 for U.S. Appl. No. 11/881,256.
Notice of allowance dated May 7, 2015 for U.S. Appl. No. 12/602,787.
Office action dated Mar. 3, 2015 for U.S. Appl. No. 14/560,194.
Office action dated May 8, 2015 for U.S. Appl. No. 13/116,370.
Notice of allowance dated Jul. 9, 2015 for U.S. Appl. No. 13/030,384.
Co-pending U.S. Appl. No. 14/811,352, filed Jul. 28, 2015.
Office action dated Sep. 16, 2015 for U.S. Appl. No. 13/116,370.
Response to office action dated Oct. 19, 2015 for U.S. Appl. No. 12/774,254.

(56) References Cited

OTHER PUBLICATIONS

Office action dated Oct. 7, 2015 for U.S. Appl. No. 13/455,005.
Office action dated Nov. 27, 2015 for U.S. Appl. No. 14/560,194.
Office action dated Jan. 20, 2016 for U.S. Appl. No. 13/455,005.
Angell James. The effects of altering mean pressure, pulse pressure and pulse frequency on the impulse activity in baroreceptor fibres from the aortic arch and right subclavian artery in the rabbit. J Physiol. Apr. 1971;214(1):65-88.
Bennetts, et al. Coronary artery baroreceptor-mediated changes in arterial pressure: a pilot study in conscious and anaesthetized sheep. Clin Exp Pharmacol Physiol. Sep. 2001; 28(9): 768-72, (an abstract).
Delfino, et al. (1997) Residual Strain Effects on the Stress Field in a Thick Wall Finite Element Model of the Human Carotid Bifurcation. Science, 30(8), 777-786.
Dilley, et al. Glomerular ultrafiltration dynamics during increased renal venous pressure. Renal Physiology. 1983; 244(6):650-F658, (an abstract).
Doty, et al. Effect of increased renal venous pressure on renal function. The Journal of Trauma: Injury, Infection, and Critical Care: Dec. 1999; 47(6):1000, (an abstract).
Feng, et al. Theoretical and electrophysiological evidence for axial loading about aortic baroreceptor nerve terminals in rats. Am J Physiol Heart Circ Physiol. Dec. 2007; 293 (6): H3659-72.
Lardenoye ,et al. Inhibition of Accelerated Atherosclerosis in Vein Grafts by Placement of External Stent in ApoE*3-Leiden Transgenic Mice. Arteriosclerosis, Thrombosis, and Vascular Biology. 2002; 22:1433.
Levenberg, et al., "Endothelial cells derived from human embryonic stem cells", PNAS Apr. 2, 2002, vol. 99, No. 7 pp. 4391-4396.
Mendelowitz, et al. (1990), Pulsatile pressure can prevent rapid baroreflex resetting. The American journal of physiology, 258(1 Pt. 2), H92-100. Retrieved from http://www.ncbi.nlm.nih.gov/pubmed/2301618.
Mendelsohn, et al. Acute hemodynamic changes during carotid artery stenting. Am J Cardiol. 1998; 82:1077-1081.
Moreau, et al. Ascorbic Acid Selectively Improves Large Elastic Artery Compliance in Postmenopausal Women. Hypertension 2005; 45: 1107.
Office action dated Jan. 3, 2013 for U.S. Appl. No. 12/774,254.
Office action dated Jan. 29, 2013 for U.S. Appl. No. 12/602,787.
Office action dated Mar. 14, 2013 for U.S. Appl. No. 13/030,384.
Office action dated Apr. 19, 2012 for U.S. Appl. No. 12/774,254.
Office action dated Jul. 17, 2013 for U.S. Appl. No. 12/602,787.
Office action dated Sep. 27, 2012 for U.S. Appl. No. 13/030,384.
Paick, et al. Implantable penile venous compression device: initial experience in the acute canine model. The Journal of Urology 1992; 148(1):188-191. (an abstract).
Riley, et al. Ultrasonic measurement of the elastic modulus of the common carotid artery. The Atherosclerosis Risk in Communities (ARIC) Study WA. 1992; 23; 952-956. Stroke.
Tang, et al. Carotid sinus nerve blockade to reduce blood pressure instability following carotid endarterectomy: a systematic review and meta-analysis. Eur J. Vasc Endovasc Surg. Sep. 2007; 34(3):304-11. (an abstract).
Ziaie,et al. An Implantable Pressure Sensor Cuff for Tonometric Blood Pressure Measurement. IEEE Solid-State Sensor and Actuator Workshop, pp. 216-219, Jun. 1998.
Office action dated Oct. 31, 2014 for U.S. Appl. No. 12/602,787.
Notice of allowance dated Aug. 2, 2016 for U.S. Appl. No. 14/560,194.
Office action dated Jun. 15, 2016 for U.S. Appl. No. 13/116,370.
International Search Report dated Feb. 3, 2010 for the PCT Application No. IL09/00932.
International search report and written opinion dated Dec. 5, 2011 for PCT/IL2011/000356.
Logan. Percutaneous mitml valve therapy. RN foundation for Cardiovascular Medicine. La Jolla. 2008; 20-22.
Office Action dated Nov. 4, 2016 for U.S. Appl. No. 14/811,352.

* cited by examiner

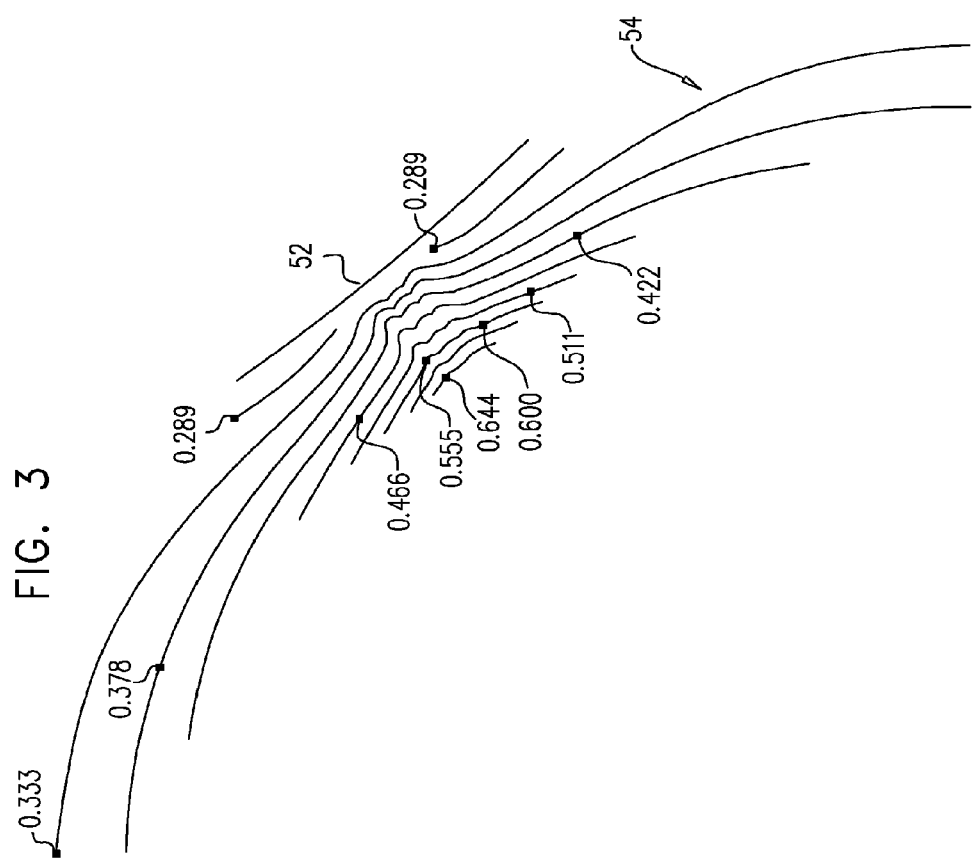

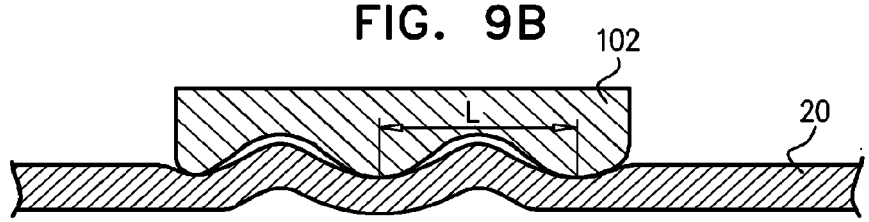
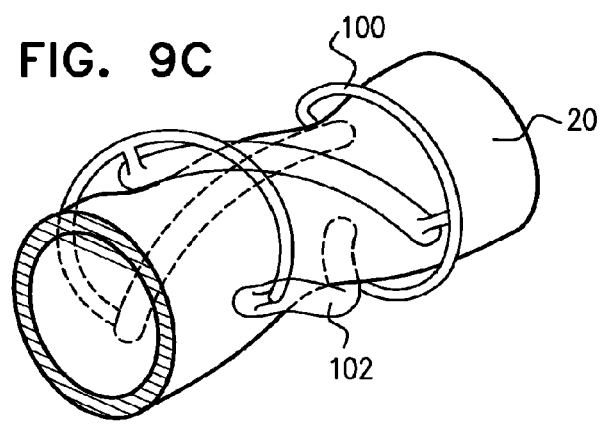
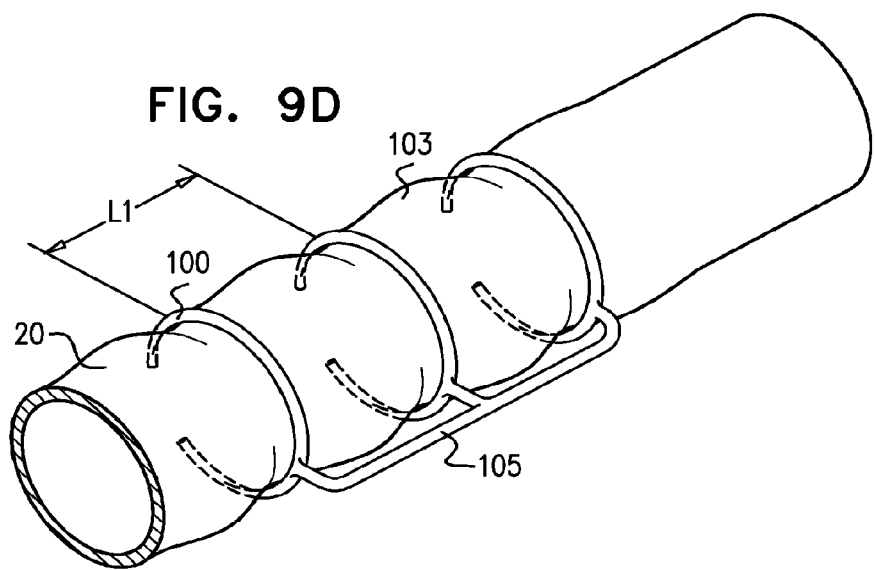

DEVICES AND METHODS FOR CONTROL OF BLOOD PRESSURE

CROSS-REFERENCES TO RELATED APPLICATIONS

The present patent application is a continuation-in-part of U.S. patent application Ser. No. 12/774,254, filed May 5, 2010, entitled "Devices and Methods for Control of Blood Pressure", which is a continuation-in-part of U.S. patent application Ser. No. 12/602,787, filed May 17, 2011, entitled "Devices and Methods for Control of Blood Pressure", which is the U.S. national phase of PCT Application No. PCT/IL2009/000932 to Gross et al. (WO 10/035271), filed Sep. 29, 2009, which claims priority from U.S. Patent Application 61/194,339, filed Sep. 26, 2008, entitled "Devices and methods for control of blood pressure"; and a continuation-in-part of U.S. patent application Ser. No. 11/881,256 (US 2008/0033501), filed Jul. 25, 2007, entitled "Elliptical element for blood pressure reduction," which is a continuation-in-part of PCT Application No. PCT/IL2006/000856 to Gross (WO 07/013065), filed Jul. 25, 2006, entitled, "Electrical stimulation of blood vessels," which claims the benefit of (a) U.S. Provisional Application 60/702,491, filed Jul. 25, 2005, entitled, "Electrical stimulation of blood vessels," and (b) U.S. Provisional Application 60/721,728, filed Sep. 28, 2005, entitled, "Electrical stimulation of blood vessels"; the entire disclosures of which are incorporated herein by reference.

FIELD OF THE INVENTION

Applications of the present invention generally relate to implanted medical apparatus. Specifically, applications of the present invention relate to apparatus and methods for reducing blood pressure.

BACKGROUND OF THE INVENTION

Hypertension is a condition from which many people suffer. It is a constant state of elevated blood pressure which can be caused by a number of factors, for example, genetics, obesity or diet. Baroreceptors located in the walls of blood vessels act to regulate blood pressure. They do so by sending information to the central nervous system (CNS) regarding the extent to which the blood vessel walls are stretched by the pressure of the blood flowing therethrough. In response to these signals, the CNS adjusts certain parameters so as to maintain a stable blood pressure.

PCT Application Publication WO 10/035,271 to Gross describes apparatus for reducing hypertension of a subject. A selective circumferential pressure applicator includes at least two surfaces that increase baroreceptor activity of the subject, by applying pressure to an artery of the subject at two or more respective non-contiguous regions around the circumference of the artery, at a longitudinal site of the artery, such that between the non-contiguous regions, at the longitudinal site (a) there is at least one region of the artery that is more relaxed than in the absence of the device, and (b) there is at least one region of the artery that is more tense than in the absence of the device. A joint couples the surfaces to each other. For at least a portion of the subject's cardiac cycle, the joint does not contact the subject's artery. Other applications are also provided.

US Patent Application Publication 2008/0033501 to Gross describes apparatus for treating hypertension of a subject. The apparatus includes an implantable element which has a non-circular shape and which is configured to reduce the hypertension by facilitating an assumption of a non-circular shape by a blood vessel in a vicinity of a baroreceptor of the subject, during diastole of the subject. Other embodiments are also described.

CVRx (Minneapolis, Minn.) manufactures the CVRx®Rheos Baroreflex Hypertension Therapy System, an implantable medical device for treating subjects with high blood pressure.

The following references may be of interest:

European Patent 0,791,341 to Demeyere et al.,

PCT Publication WO 02/26314 to Kieval, PCT Publication WO 03/076008 to Shalev, PCT Publication WO 03/082080 to Bolea, PCT Publication WO 03/082403 to Kieval, PCT Publication WO 04/073484 to Gross et al., PCT Publication WO 05/084389 to Kieval, PCT Publication WO 05/097256 to Rossing, PCT Publication WO 06/012033 to Rossing, PCT Publication WO 06/012050 to Rossing, PCT Publication WO 06/032902 to Caro et al., PCT Publication WO 06/041664 to Kieval, PCT Publication WO 06/125163 to Hagen, PCT Publication WO 07/013,065 to Gross, PCT Publication WO 07/047,152 to Rossing, PCT Publication WO 07/080,595 to Levi, PCT Publication WO 07/114,860 to Rossing, PCT Publication WO 07/118,090 to Rossing, PCT Publication WO 07/136,850 to Rossing, PCT Publication WO 07/136,851 to Rossing, PCT Publication WO 08/039,982 to Kieval, PCT Publication WO 08/083,120 to Hagen, PCT Publication WO 08/083,235 to Cates, WO 09/018,394 to Schneider US Patent Application Publication 2003/0060858 to Kieval et al., US Patent Application Publication 2003/0199806 to Kieval, US Patent Application Publication 2004/0010303 to Bolea, US Patent Application Publication 2004/0019364 to Kieval, US Patent Application Publication 2004/0106976 to Bailey et al., US Patent Application Publication 2004/0193092 to Deal, US Patent Application Publication 2004/0254616 to Rossing, US Patent Application Publication 2005/0027346 to Arkusz et al., US Patent Application Publication 2005/0033407 to Weber et al., US Patent Application Publication 2005/0096710 to Kieval, US 2005/0143765 to Bachmann, US 2005/0143766 to Bachmann, US 2005/0149128 to Heil, Jr., US 2005/0149131 to Libbus, US 2005/0149143 to Libbus, US Patent Application Publication 2005/0154418 to Kieval et al., US Patent Application Publication 2005/0203610 to Tzeng, US Patent Application Publication 2005/0232965 to Falotico, US Patent Application Publication 2005/0251212 to Kieval, US Patent Application Publication 2005/0261257 to Vermeer, US Patent Application Publication 2006/0004417 to Rossing, US Patent Application Publication 2006/0004420 to Rossing, US Patent Application Publication 2006/0004430 to Rossing, US Patent Application Publication 2006/0074453 to Kieval et al., US 2006/0089678 to Shalev, US Patent Application Publication 2006/0111626 to Rossing, US 2006/0241334 to Dubi, US Patent Application Publication 2006/0265038 to Hagen, US 2006/0276852 to Demarais, US Patent Application Publication 2006/0293712 to Kieval, US Patent Application Publication 2007/0021790 to Kieval, US Patent Application Publication 2007/0021792 to Kieval, US Patent Application Publication 2007/0021794 to Kieval, US Patent Application Publication 2007/0021796 to Kieval, US Patent Application Publication 2007/0021797 to Kieval, US Patent Application Publication 2007/0021798 to Kieval, US Patent Application Publication 2007/0021799 to Kieval, US Patent Application Publication 2007/0038255 to Kieval, US Patent Application Publication 2007/0038259 to Kieval, US Patent Application Publication 2007/0038260 to Kieval, US Patent Application Publication 2007/0038261 to Kieval, US Patent Application Publication 2007/0038262 to Kieval, US Patent Application Publication 2007/0049989 to Rossing, US 2007/0055296 to Stergiopulos, US Patent Application Publication 2007/0060972 to Kieval, US Patent Application Publication 2007/0106340 to Bolea, US 2007/0142879 to Greenberg, US Patent Application Publication 2007/0156198 to Rossing, US Patent Application Publication 2007/0156201 to Rossing, US Patent Application Publication 2007/0167984 to Kieval, US Patent Application Publication 2007/0185542 to Bolea, US Patent Application Publication 2007/0185543 to Rossing, US 2007/0187255 to Ogasawara, US 2007/0250085 to Bachmann, US Patent Application Publication 2007/0276442 to Hagen, US Patent Application Publication 2007/0276459 to Rossing, US Patent Application Publication 2007/0282385 to Rossing, US Patent Application Publication 2008/0004673 to Rossing, US Patent Application Publication 2008/0009916 to Rossing, US Patent Application Publication 2008/0009917 to Rossing, US 2008/0027469 to Bachmann, US Patent Application Publication 2008/0046054 to Hjelle, US Patent Application Publication 2008/0051767 to Rossing, US Patent Application Publication 2008/0082137 to Kieval, US Patent Application Publication 2008/0097540 to Bolea, US 2008/0132966 to Levin, US Patent Application Publication 2008/01401671 to Hagen, US Patent Application Publication 2008/0154349 to Rossing, US Patent Application Publication 2008/0161865 to Hagen, US Patent Application Publication 2008/0161887 to Hagen, US Patent Application Publication 2008/0167690 to Cody, US Patent Application Publication 2008/0167693 to Kieval, US Patent Application Publication 2008/0167694 to Bolea, US Patent Application Publication 2008/0167696 to Cates, US Patent Application Publication 2008/0167699 to Kieval, US Patent Application Publication 2008/0171923 to Bolea, US Patent Application Publication 2008/0172101 to Bolea, US Patent Application Publication 2008/0172104 to Kieval, US 2009/0248138 to Golesworthy U.S. Pat. No. 3,650,277 to Sjostrand et al., U.S. Pat. No. 4,201,219 to Bozal Gonzalez, U.S. Pat. No. 4,791,931 to Slate, U.S. Pat. No. 4,938,766 to Jarvik, U.S. Pat. No. 5,437,285 to Verrier, U.S. Pat. No. 5,669,924 to Shaknovich, U.S. Pat. No. 5,707,400 to Terry, Jr., U.S. Pat. No. 5,727,558 to Hakki, U.S. Pat. No. 6,322,553 to Vito, U.S. Pat. No. 6,375,666 to Mische, U.S. Pat. No. 6,442,424 to Ben-Haim, U.S. Pat. No. 6,522,926 to Kieval et al., U.S. Pat. No. 6,554,856 to Doorly, U.S. Pat. No. 6,575,994 to Marin et al., U.S. Pat. No. 6,616,624 to Kieval, U.S. Pat. No. 6,669,686 to Singh, U.S. Pat. No. 6,681,136 to Schuler, U.S. Pat. No. 6,764,498 to Mische, U.S. Pat. No. 6,899,669 to Vito, U.S. Pat. No. 6,957,106 to Schuler, U.S. Pat. No. 6,974,445 to Stergiopulos, U.S. Pat. No. 6,850,801 to Kieval, U.S. Pat. No. 6,972,031 to Braginsky, U.S. Pat. No. 6,985,774 to Kieval, U.S. Pat. No. 7,044,981 to Liu et al., U.S. Pat. No. 7,060,080 to Bachmann, U.S. Pat. No. 7,128,750 to Stergiopulos, U.S. Pat. No. 7,158,832 to Kieval, U.S. Pat. No. 7,194,313 to Libbus, U.S. Pat. No. 7,218,964 to Hill, U.S. Pat. No. 7,238,191 to Bachmann, U.S. Pat. No. 7,300,449 to Mische, U.S. Pat. No. 7,373,204 to Gelfand, U.S. Pat. No. 7,389,149 to Rossing, U.S. Pat. No. 7,395,119 B2 to Hagen, U.S. Pat. No. 7,647,931 to Pflueger "Ascorbic Acid Selectively Improves Large Elastic Artery Compliance in Postmenopausal Women," Moreau K. L., Hypertension 2005; 45:1107

"Carotid sinus nerve blockade to reduce blood pressure instability following carotid endarterectomy: a systematic review and meta-analysis," Tang T. Y., Eur J Vasc Endovasc Surg. 2007 September; 34(3):304-11

"Coronary artery baroreceptor-mediated changes in arterial pressure: a pilot study in conscious and anaesthetized sheep," Bennetts J. S., Clin Exp Pharmacol Physiol. 2001 September; 28(9):768-72

"Effect of increased renal venous pressure on renal function," Doty J. M., The Journal of Trauma: Injury, Infection, and Critical Care: December 1999, Volume 47, Issue 6, p 1000.

"Glomerular ultrafiltration dynamics during increased renal venous pressure," J. R. Dilley, AJP—Renal Physiology, Vol 244, Issue 6 650-F658.

"Implantable penile venous compression device: initial experience in the acute canine model," Paick J., The Journal of Urology 1992, Vol. 148, No. 1, pp. 188-191

"Inhibition of accelerated atherosclerosis in vein grafts by placement of external stent in ApoE*3-Leiden transgenic mice," Lardenoye et al., Arteriosclerosis, Thrombosis, and Vascular Biology. 2002; 22:1433

"On the excitation mechanism of the carotid baroceptors," Landgren S., Acta Physiol Scand. 1952 Jul. 17; 26(1):1-34

"Percutaneous Mitral Valve Therapy," presented by Julie Logan, RN Foundation for Cardiovascular Medicine La Jolla "The effects of altering mean pressure, pulse pressure and pulse frequency on the impulse activity in baroreceptor fibres from the aortic arch and right subclavian artery in the rabbit," Angell James J E, J. Physiol. 1971 April; 214(1): 65-88

"Theoretical and electrophysiological evidence for axial loading about aortic baroreceptor nerve terminals in rats," Feng B, Am J Physiol Heart Circ Physiol. 2007 December; 293(6):H3659-72

SUMMARY OF THE INVENTION

For some applications, a subject's hypertension is treated by modulating the subject's baroreceptor activity. Mechanical and other forces are applied directly or indirectly to one or more of the subject's arteries in order to modulate the baroreceptor response to the blood pressure. The forces are typically applied to arteries that are rich in baroreceptors, for example, the carotid arteries, the aorta, the subclavian arteries and/or arteries of the brain. For some applications, the forces are applied to other regions of the body that contain baroreceptors, such as the atria.

Baroreceptors measure strain, which, in the case of a circular vessel, depends on the pressure and the radius of the vessel. As pressure increases, the stress exerted on the wall increases, thereby increasing the strain in the vessel wall. Equation 1 relates the wall stress σ in a thin walled tube, to internal pressure p, internal radius r, and wall thickness t.

$$\sigma = pr/2t \qquad \text{[Equation 1]}$$

In a hypertensive patient, the pressure-strain relationship is typically shifted to higher pressures, such that the artery is subject to a given strain at a higher blood pressure than the blood pressure in a healthy vessel that would give rise to the given strain. Thus, the baroreceptors are activated at a higher blood pressure in a hypertensive patient than they are in a healthy patient. The devices described herein typically cause the pressure-strain curve to shift back to lower pressures.

The inventors hypothesize that, at constant pressure, by increasing the radius of curvature of a region of an arterial wall, the strain in the region of the wall may be increased. Thus, the baroreceptor nerve endings in the region (which are typically disposed between the medial and adventitial layers of the artery, as described in further detail hereinbelow) experience greater strain, ceteris paribus. The intravascular devices described herein typically increase the radius of curvature of regions of the arterial wall, but do not cause a substantial decrease in the cross-section of the artery (and, typically, cause an increase in the cross-section of the artery), thereby maintaining blood flow through the artery. For some applications, the devices change the shape of the artery such that the artery is less circular than in the absence of the device, thereby increasing the radius of curvature of sections of the arterial wall.

Typically, the devices described herein change the shape of the artery by being placed inside or outside the artery, but by maintaining less than 360 degrees of contact with the surface of the artery at any given site along the length of the artery. Further typically, contact between the device and the artery is limited to several (e.g., two to six, or three to six) contact regions around the circumference of the artery, and is generally minimized. Still further typically, the device is placed inside the artery such that there are several regions at which the device does not contact the artery, each of the non-contact regions being contiguous, and defining an angle that is greater than 10 degrees around the longitudinal axis of the artery, as described in further detail hereinbelow. This may be beneficial for the following reasons:

(1) A greater area of the artery pulsates in response to pressure changes than if the device were to maintain a greater degree of contact with the vessel wall. It is generally desirable to allow at least a portion of the vessel to pulsate freely. This is because pulsation of the vessel over the course of the cardiac cycle typically activates and maintains normal functioning of the baroreceptors. For some applications, baroreceptor activity in the portions of the vessel that are in contact with the device may be reduced, since the movement of those portions in response to changes in blood pressure is reduced. Therefore, for some applications, contact between the device and the artery is minimized.

(2) A smaller metal to lumen ratio typically causes less reactive growth of endothelial and smooth muscle cells. Typically, reducing this reactive growth reduces the chances of stenosis being caused by the device. Further typically, reducing this reactive growth facilitates explantation, and/or movement of the device, when desired.

For some applications the devices described herein are implanted temporarily, and are subsequently removed. For example, one of the devices described herein may be implanted for a period of less than one month, e.g., less than one week. Temporary implantation of the devices is typically used to treat an acute condition of the subject. For some applications, the shape of the artery in which the device is implanted is permanently altered by temporarily implanting the device.

Typically, the devices described herein are implanted inside or outside of the subject's carotid artery, e.g., at the carotid sinus. In accordance with respective embodiments, the devices are implanted bilaterally, or inside or outside of only one of the subject's carotid arteries. Alternatively or additionally, the devices are placed inside or outside of a different artery, e.g., the aorta or the pulmonary artery.

The devices are typically self-anchoring and structurally stable. Further typically, the devices are passive devices, i.e., subsequent to the devices being implanted inside or outside of the artery, the devices act to increase baroreceptor sensitivity without requiring electrical or real-time mechanical activation.

There is therefore provided, in accordance with some applications of the present invention, a method, including:
  identifying a subject as suffering from hypertension; and
  in response to the identifying,
    (a) increasing a radius of curvature of a first set of at least three regions of an arterial wall of the subject at a given longitudinal location, while
    (b) allowing the first set of regions of the arterial wall to pulsate, by
  implanting a device inside the artery at the longitudinal location such that the device applies pressure to the arterial wall at a second set of at least three regions of the artery, but does not contact the first set of regions, the first set of regions and the second set of regions alternating with each other.

For some applications, implanting the device includes increasing strain in the arterial wall at both the first and the second set of regions, relative to the strain in the arterial wall when the device is absent from the artery.

For some applications, implanting the device includes increasing a cross-sectional area of the artery.

For some applications, implanting the device includes implanting a device such that the second set of regions includes three to six regions at which the device applies pressure to the arterial wall.

For some applications, implanting the device includes implanting the device for less than one month.

For some applications, implanting the device includes implanting the device inside a carotid artery of the subject.

For some applications, implanting the device includes implanting the device inside a pulmonary artery of the subject.

For some applications, implanting the device includes implanting the device inside an aorta of the subject.

For some applications, implanting the device includes placing the device inside the artery and allowing the device to become self-anchored to the artery.

For some applications, implanting the device includes implanting a device having a total cross-sectional area of less than 5 sq mm.

For some applications, implanting the device includes implanting a device having a total cross-sectional area of less than 0.5 sq mm.

For some applications, increasing the radius of curvature of the first set of at least three regions of the arterial wall includes increasing a systolic radius of curvature at the regions to more than 1.1 times the systolic radius of curvature of the arterial wall when the device is absent from the artery.

For some applications, increasing the radius the curvature of the first set of at least three regions of the arterial wall includes increasing a systolic radius of curvature at the regions to more than two times the systolic radius of curvature of the arterial wall when the device is absent from the artery.

For some applications, increasing the radius the curvature of the first set of at least three regions of the arterial wall includes increasing a systolic radius of curvature at the regions to more than twenty times the systolic radius of curvature of the arterial wall when the device is absent from the artery.

For some applications, implanting the device includes implanting the device such that each of the regions of the first set of regions is a contiguous region that is able to pulsate, each of the contiguous regions encompassing an angle around a longitudinal axis of the artery of greater than 10 degrees.

For some applications, implanting the device includes implanting the device such that each of the regions of the first set of regions is a contiguous region that is able to pulsate, each of the contiguous regions encompassing an angle around the longitudinal axis of the artery of greater than 20 degrees.

For some applications, implanting the device includes implanting the device such that each of the regions of the first set of regions is a contiguous region that is able to pulsate, each of the contiguous regions encompassing an angle around the longitudinal axis of the artery of greater than 50 degrees.

For some applications, implanting the device includes implanting the device such that the first set of regions encompass more than 20 percent of a circumference of the arterial wall at the longitudinal location, during systole of the subject.

For some applications, implanting the device includes implanting the device such that the first set of regions encompass more than 80 percent of the circumference of the arterial wall at the longitudinal location, during systole of the subject.

There is further provided, in accordance with some applications of the present invention, apparatus for treating hypertension of a subject, including:
an implantable device shaped to define at least three separate artery-contacting surfaces, and configured to:
  (a) increase a radius of curvature of a wall of the artery at a first set of at least three regions of the arterial wall at a given longitudinal location, while
  (b) allowing the first set of regions of the arterial wall to pulsate at the longitudinal location, by
  the device being implanted inside the artery at the longitudinal location such that the artery-contacting surfaces contact a second set of at least three regions of the arterial wall, but do not contact the first set of regions of the arterial wall, the first set of regions and the second set of regions alternating with each other.

For some applications, the device is configured such that as the artery-contacting surface apply increasing pressure to the arterial wall, a cross-sectional area of the artery increases.

For some applications, the device is configured to increase strain in the arterial wall at both the first and the second set of regions, relative to the strain in the arterial wall when the device is absent from the artery.

For some applications, the device is configured to increase a cross-sectional area of the artery.

For some applications, the artery-contacting surfaces includes three to six artery contacting surfaces.

For some applications, the device is configured to be implanted inside the artery for less than one month.

For some applications, the device is configured to be implanted inside a carotid artery of the subject.

For some applications, the device is configured to be implanted inside a pulmonary artery of the subject.

For some applications, the device is configured to be implanted inside an aorta of the subject.

For some applications, the device is configured to become self-anchored to the artery.

For some applications, the device has a total cross-sectional area of less than 5 sq mm.

For some applications, the device has a total cross-sectional area of less than 0.5 sq mm.

For some applications, edges of at least two adjacent artery-contacting surfaces define an angle around a longitudinal axis of the device of greater than 10 degrees.

For some applications, the edges of the two artery-contacting surfaces define an angle around the longitudinal axis of the device of greater than 20 degrees.

For some applications, the edges of the two artery-contacting surfaces define an angle around the longitudinal axis of the device of greater than 50 degrees.

There is additionally provided, in accordance with some applications of the present invention, a method, including:
identifying a subject as suffering from hypertension; and
in response to the identifying,
  (a) increasing strain at a first set of regions of an arterial wall of the subject at a given longitudinal location,
  (b) while maintaining, at a given stage in a cardiac cycle of the subject, a cross-section of the artery at the longitudinal location that is at least 20 percent of the cross-section of the artery at the longitudinal location, at the given stage of the cardiac cycle, when the device is absent, by
implanting a device outside the artery at the longitudinal location such that the device applies pressure to the arterial wall at the first set of regions of the arterial wall, but does not contact the arterial wall at at least a second set of regions of the arterial wall at the longitudinal location, the first set of regions and the second set of regions alternating with each other.

For some applications, implanting the device includes implanting the device outside a carotid artery of the subject.

For some applications, implanting the device includes implanting the device outside a pulmonary artery of the subject.

For some applications, implanting the device includes implanting the device outside an aorta of the subject.

For some applications, maintaining the cross-section of the artery that is at least 20 percent of the cross-section of the artery at the longitudinal location when the device is absent, includes maintaining an internal diameter of the artery, in the presence of the device, that is at least 30 percent of the diameter of the artery in the absence of the device.

For some applications, maintaining the cross-section of the artery that is at least 20 percent of the cross-section of the artery at the longitudinal location when the device is absent, includes maintaining a rate of blood flow through the artery that is more than 70 percent of the rate of blood flow through the artery in the absence of the device.

For some applications, maintaining the rate of blood flow through the artery that is more than 70 percent of the rate of blood flow through the artery in the absence of the device, includes maintaining a rate of blood flow through the artery that is more than 90 percent of the rate of blood flow through the artery in the absence of the device.

For some applications, implanting the device includes implanting the device such that the arterial wall is able to pulsate at each of the second set of regions.

For some applications, implanting the device includes implanting a device outside the artery at the longitudinal location such that the device applies pressure to the arterial wall at a first set of three to six regions of the artery, but does not contact the artery at a second set of three to six regions of the artery.

For some applications, implanting the device includes implanting a device outside the artery at the longitudinal location such that the device does not contact the artery at at least the second set of regions of the artery, each of the second set of regions being contiguous, and encompassing an angle around a longitudinal axis of the artery of greater than 10 degrees.

For some applications, implanting the device includes implanting a device such that each of the second set of regions encompasses an angle around the longitudinal axis of the artery of greater than 20 degrees.

For some applications, implanting the device includes implanting a device such that each of the second set of regions encompasses an angle around the longitudinal axis of the artery of greater than 50 degrees.

For some applications, implanting the device includes implanting the device such that the device encompasses less than 90 percent of a circumference of the artery.

For some applications, implanting the device includes implanting the device such that the device encompasses less than 70 percent of the circumference of the artery.

There is additionally provided, in accordance with some applications of the present invention, apparatus for treating hypertension of a subject, including:

an implantable device shaped to define a single pair of artery-contacting surfaces, and configured to:
  (a) increase a radius of curvature of the artery at a first set of two regions of the artery at a given longitudinal location, while
  (b) allowing the first set of regions of the artery to pulsate at the longitudinal location, by
  the device being implanted inside the artery at the longitudinal location such that the artery-contacting surfaces contact a second set of two regions of the artery, but at no point during a cardiac cycle of the subject does the device contact the first set of regions, the first set of regions and the second set of regions alternating with each other.

For some applications, the device is configured such that when the device is implanted in the artery no portion of the device intersects a longitudinal axis of the artery.

For some applications, the device further includes a joint configured to couple the artery-contacting surfaces to one another, and the joint is disposed asymmetrically with respect to centers of the artery-contacting surfaces.

The present invention will be more fully understood from the following detailed description of embodiments thereof, taken together with the drawings, in which:

BRIEF DESCRIPTION OF THE DRAWINGS

FIG. 3 is a contour plot of the strain in the wall of an artery, an extravascular device having been implanted outside the wall, in accordance with some applications of the present invention;

FIGS. 9A-D are schematic illustrations of extravascular devices placed around an artery, in accordance with some applications of the present invention;

DETAILED DESCRIPTION OF THE EMBODIMENTS

Figure 1:
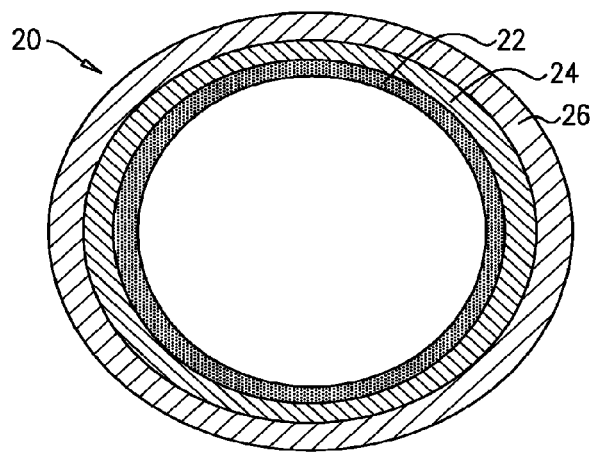
FIG. 1 is a cross-sectional illustration of an artery.

Reference is now made to FIG. 1, which is a cross-sectional illustration of an artery 20. The arterial wall includes three layers 22, 24, and 26, which are called, respectively, the intima, the media, and the adventitia. For some applications of the present invention, an intravascular device is placed inside an artery, baroreceptors being disposed at the interface between adventitia 26 and media 24 of the artery. The device causes the curvature of the arterial wall to flatten in some regions of the circumference of the arterial wall, thereby causing the baroreceptors to become stretched, while allowing the regions to pulsate over the course of the subject's cardiac cycle.

Figure 2A:
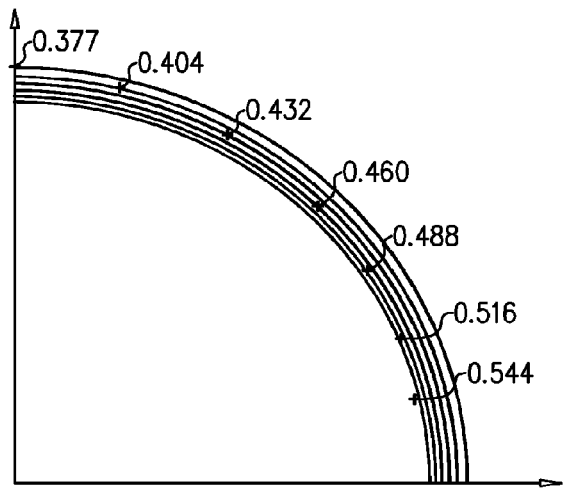
FIGS. 2A-B are contour plots of the strain in the wall of an artery, respectively, when the artery does have and does not have inserted therein an intravascular device, in accordance with some applications of the present invention.
Figure 2B:
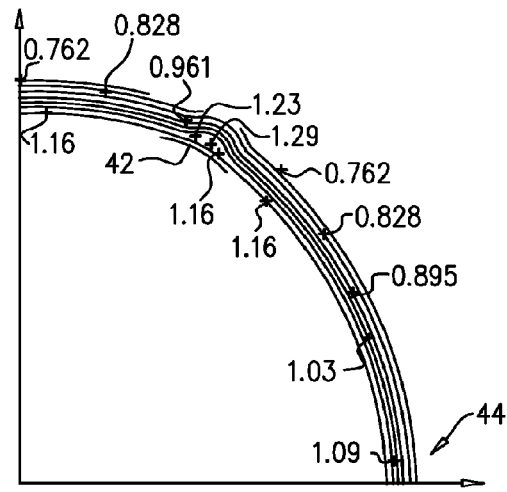

Reference is now made to FIGS. 2A and 2B, which are contour plots of the strain in the top right quarter of an arterial wall, in the absence of an intravascular device (FIG. 2A) and in the presence of an intravascular device (FIG. 2B), analyzed and/or provided in accordance with some applications of the present invention. The contour plot in FIG. 2B was generated for a device (e.g., as shown hereinbelow in FIGS. 7A-B) having four elements, each of which contacts the arterial wall at a contact region 42. The contour plots shown in FIGS. 2A-B are computer simulations of the strain in the wall of an artery, at a blood pressure of 100 mmHg, the artery having a radius of 3 mm, and a wall thickness of 0.6 mm. The scope of the present application includes intravascular devices having different structures from that used to generate FIG. 2B, as would be obvious to one skilled in the art.

As seen in FIGS. 2A-B, relative to the strain in the arterial wall in the absence of an intravascular device, the intravascular device causes there to be increased strain in the arterial wall both (a) in the vicinity of contact regions 42, at which the arterial wall becomes more curved than in the absence of the device, and (b) in flattened regions 44 of the wall, in which regions the arterial wall is flatter than it is in the absence of the device. Thus, the intravascular device increases the strain in the arterial wall even in regions of the arterial wall which are able to pulsate, i.e., flattened regions 44. The increased strain in the flattened regions relative to the strain in the wall in the absence of the intravascular device is due to the increased radius of curvature of the flattened regions of the wall.

Reference is now made to FIG. 3, which is a contour plot of the strain in the top right quarter of an arterial wall, in the presence of an extravascular device, in accordance with some applications of the present invention. The contour plot in FIG. 3 was generated for a device having four elements that contact the artery at four contact regions 52. However, the scope of the present invention includes extravascular devices having different structures, as described hereinbelow. For example, an extravascular device may provide three to six contact regions. The contour plot shown in FIG. 3 is a computer simulation of the strain in the wall of an artery, at a blood pressure of 100 mmHg, the artery having a radius of 3 mm, and a wall thickness of 0.6 mm.

As may be observed by comparing FIG. 3 to FIG. 2A, the extravascular device causes there to be strain in the arterial wall in the vicinity of contact regions 52, at which the arterial wall becomes more curved than in the absence of the device. Furthermore, it may observed that the strain at non-contact regions 54 of the wall is lower than in the absence of the device. The extravascular device typically breaks the circumferential symmetry of the arterial strain by applying force at discrete points or surfaces around the sinus. For some applications, the extravascular device increases the strain in certain regions of the arterial wall, and decreases the strain in other regions of the arterial wall, while maintaining the average strain almost unchanged or even slightly reduced with respect to the strain in the wall in the absence of the device. For some applications, the extravascular device increases the strain in the arterial wall even at non-contact regions 54, by causing the non-contact regions to become more curved than in the absence of the device.

Figure 4:
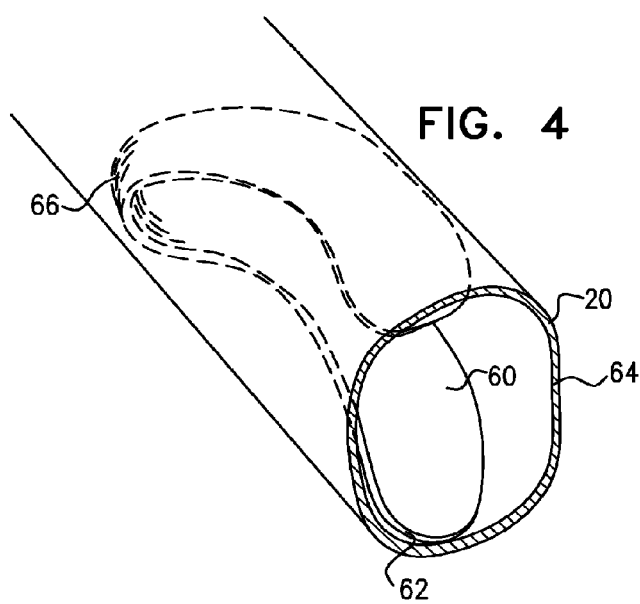
FIG. 4 is a schematic illustration of an intravascular device for placing inside an artery of a subject suffering from hypertension, in accordance with some applications of the present invention.

Reference is now made to FIG. 4, which is a schematic illustration of an intravascular device 60 for placing inside artery 20 of a subject suffering from hypertension, in accordance with some applications of the present invention. As shown, device 60 contacts the arterial wall at two contact regions 62. At the contact regions, device 60 pushes the arterial wall outward, thereby flattening non-contact regions 64 of the arterial wall between the contact regions. Typically, non-contact regions 64 are flattened, or partially flattened during diastole of the subject, but expand during systole such that they become more curved than during diastole. Therefore, strain in the flattened regions of the arterial wall is increased. However, the flattened regions still pulsate over the course of the subject's cardiac cycle in the presence of device 60.

As shown, device 60 is shaped such that the device substantially does not reduce blood flow. Typically, device 60 is shaped such that no portion of the device intersects the longitudinal axis of the artery. For example, as shown, contact surfaces of the device (which contact the arterial wall at contact regions 60) are coupled to each other by a joint 66 that does not intersect the longitudinal axis of the artery. The joint is disposed asymmetrically with respect to centers of the contact surfaces of the device.

Figure 5A:
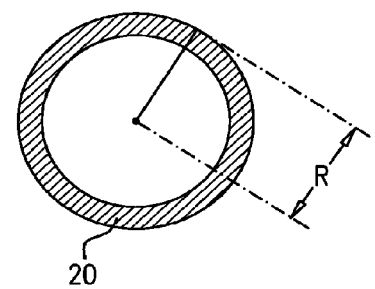
FIGS. 5A-B are schematic illustrations of an artery, showing the radius of curvature of the artery, respectively, before and after placement of the device shown in FIG. 4, in accordance with some applications of the present invention.
Figure 5B:
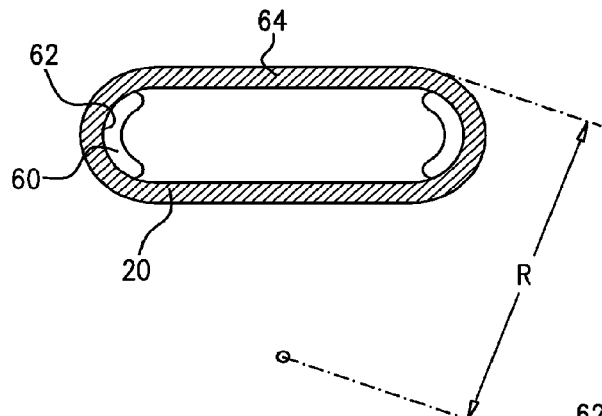

Reference is now made to FIGS. 5A-B, which are schematic illustrations of an artery, showing the radius R of artery 20, respectively, before and after placement of the device 60 shown in FIG. 4, in accordance with some applications of the present invention. It may be observed that, for some applications, insertion of device 60 increases the systolic radius of curvature of the artery at non-contact regions 64, for example, such that the radius of curvature at non-contact regions 64 is more than 1.1 times (e.g., twice, or more than twenty times) the systolic radius of curvature of regions 64 in the absence of device 60, ceteris paribus. For some applications, device 60 causes the radius of curvature of at least a portion of a non-contact region to become infinite, by flattening the non-contact regions. For example, the center of non-contact region 64 in FIG. 5B has an infinite radius of curvature.

For some applications, device 60 increases the systolic radius of curvature of the artery at non-contact regions 64 in the aforementioned manner, and increases the systolic cross-sectional area of the artery by more than five percent (e.g., ten percent), relative to the systolic cross-sectional area of the artery in the absence of device 60.

In accordance with the description hereinabove, by flattening non-contact regions 64 of the wall of artery 20, device 60 causes increased strain in regions 64, thereby causing an increase in baroreceptor firing at regions 64. Alternatively or additionally, device 60 causes increased baroreceptor firing at contact regions 62, by deforming the arterial wall at the contact regions.

Typically, device 60 exerts a force on artery 20, such that, during systole when the artery is in the stretched configuration shown in FIG. 5B, non-contact regions 64 comprise more than ten percent, e.g., more than 20 percent, of the circumference of the arterial wall at longitudinal sites at which device 60 stretches the artery. For some applications, during systole, non-contact regions 64 comprise more than 60 percent, e.g., more than 80 percent, of the circumference of the arterial wall at longitudinal sites at which device 60 stretches the artery.

Figure 5C:
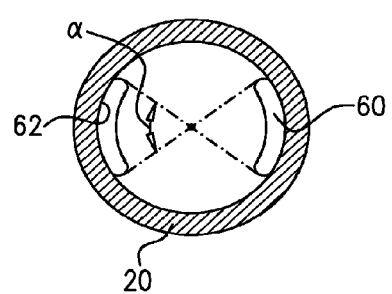
FIG. 5C is a schematic illustration of the device of FIG. 4 disposed inside the artery, without stretching the artery, for illustrative purposes.

Reference is now made to FIG. 5C, which shows device disposed inside artery 20, but without the device stretching artery 20. FIG. 5C is for illustrative purposes, since typically once device 60 is inserted into the artery, the device will stretch the artery, as shown in FIG. 5B. FIG. 5C demonstrates that the device contacts the walls of the artery at contact regions 62 at less than 360 degrees of the circumference of the artery at any longitudinal point along artery 20 (e.g., at the cross-section shown in FIGS. 5A-C). As shown in FIG. 5C, each of the contact regions 62 encompasses an angle alpha of the circumference of the artery, such that the contact that device 60 makes with the walls of the artery encompasses two times alpha degrees. For devices that contact the artery at more than two contact regions, the contact that the device makes with the walls of the artery encompasses an angle that is a correspondingly greater multiple of alpha degrees. Typically, device 60 (and the other intravascular devices described herein) contacts the walls of the artery at less than 180 degrees (e.g., less than 90 degrees) of the circumference of the artery at any longitudinal site along the artery. Typically, device 60 contacts the walls of the artery at more than 5 degrees (e.g., more than 10 degrees) of the circumference of the artery at any longitudinal site along the artery. For example, device 60 may contact the walls of the artery at 5-180 degrees, e.g., 10-90 degrees, at a given longitudinal site.

Figure 6A:
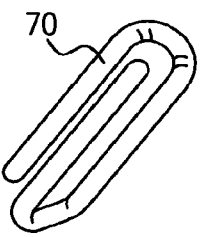
FIGS. 6A-B are schematic illustrations of, respectively, a device, and the device implanted inside an artery, in accordance with some applications of the present invention.
Figure 6B:
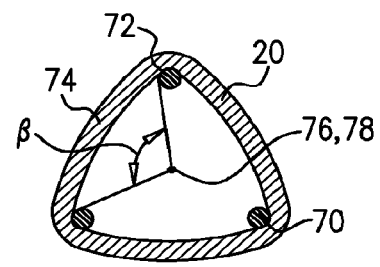

Reference is now made to FIGS. 6A-B, which are schematic illustrations of, respectively, a device 70, and device 70 implanted inside artery 20, in accordance with some applications of the present invention. Device 70 contacts the wall of the artery at three contact regions 72, thereby increasing the radius of curvature (i.e., flattening) of non-contact regions 74 of the artery that are between the contact regions. The flattened non-contact regions and the contact regions alternate with each other. The flattened non-contact regions are typically able to pulsate over the course of the subject's cardiac cycle, as described hereinabove. As shown in FIG. 6B, each contiguous non-contact region at a given longitudinal site of the artery, encompasses an angle beta around a longitudinal axis 76 of the artery. For some devices (e.g., device 70, and device 90 described hereinbelow with reference to FIGS. 8A-B), the angle beta is also defined by the angle that edges of adjacent contact regions of the device define around longitudinal axis 78 of the device. When the device is placed in the artery longitudinal axis 78 of the device is typically aligned with longitudinal axis 76 of the artery. Typically, angle beta is greater than 10 degree, e.g., greater than 20 degree, or greater than 50 degrees. Further typically, angle beta is less than 180 degrees, e.g., less than 90 degrees. For some applications angle beta is 10-180 degree, e.g., 20-90 degrees. Typically, each of the contiguous non-contact regions is able to pulsate.

Figure 7A:
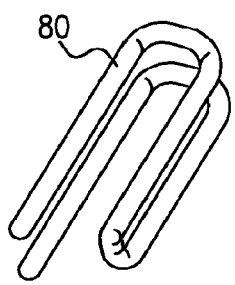
FIGS. 7A-B are schematic illustrations of, respectively, another device, and the device implanted inside an artery, in accordance with some applications of the present invention.
Figure 7B:
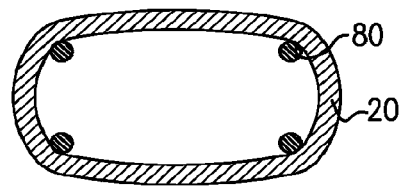

Reference is now made to FIGS. 7A-B, which are schematic illustrations of, respectively, a device 80, and device 80 implanted inside artery 20, in accordance with some applications of the present invention. Device 80 contacts the wall of the artery at four contact regions, thereby flattening the non-contact regions of the artery that are between the contact regions. Each contiguous non-contact region at a given longitudinal site of the artery, encompasses an angle beta around the longitudinal axis of the artery, angle beta being as described hereinabove.

Figure 8A:
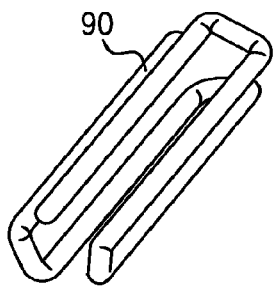
FIGS. 8A-B are schematic illustrations of, respectively, a further device, and the device implanted inside an artery, in accordance with some applications of the present invention.
Figure 8B:
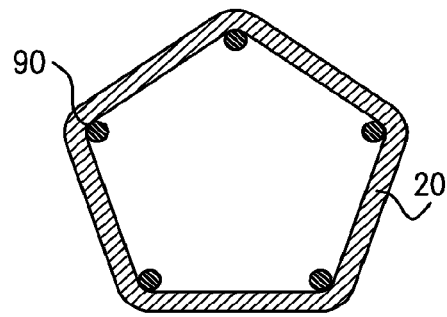

Reference is now made to FIGS. 8A-B, which are schematic illustrations of, respectively, a device 90, and device 90 implanted inside artery 20, in accordance with some applications of the present invention. Device 90 contacts the wall of the artery at five contact regions, thereby flattening the non-contact regions of the artery that are between the contact regions. Each contiguous non-contact region at a given longitudinal site of the artery, encompasses an angle beta around the longitudinal axis of, angle beta being as described hereinabove.

Apart from the fact that devices 70, 80, and 90 contact the artery at, respectively three, four, and five contact regions, devices 70, 80, and 90 function in a generally similar manner to each other, and to device 60, described with reference to FIGS. 4 and 5A-C. For example, devices 70, 80, and 90 typically contact the arterial wall around substantially less than 360 degrees of the circumference of the artery, for example, around 10-90 degrees, or around an angle as described hereinabove with reference to FIGS. 5A-C. Furthermore, devices 70, 80, and typically increase the cross-sectional area of the artery relative to the cross-sectional area of the artery in the absence of the device.

For some applications, a device having three or more contact regions with the arterial wall, for example, as shown in FIGS. 6A-8B, is used. It is noted that since device 60 (shown in FIG. 4) contacts the artery at two contact points, as the device applies increasing pressure to the artery, it will, at a given stage, decrease the cross-section of the artery, as the artery becomes increasingly elliptical. By contrast, devices 70, 80, and 90, which contact the artery at three or more contact points, increase the cross-section of the artery, as they apply increasing pressure to the wall of the artery. Thus, for some applications, a device with three or more contact regions is used in order that the cross-sectional area of the artery is increased as the force which the device exerts on the wall increases, as compared with a device with only two contact regions.

Although devices that contact artery 20 at two, three, four and five contact regions have been described, the scope of the present invention includes devices that contact the artery at a different number of contact regions, and/or that have different structures from those shown, mutatis mutandis.

The intravascular devices described herein are generally shaped such that the devices contact the intravascular wall at relatively small contact regions, and provide relatively large contiguous non-contact regions, which are able to pulsate due to the subject's cardiac cycle.

The devices are typically shaped such that the total contact region that the device makes with the arterial wall at any longitudinal point along the artery is less than 2 mm, e.g., less than 0.5 mm. The contact region is usually larger than 0.05 mm, e.g., greater than 0.2 mm. For example, the contact region may be 0.05-2 mm, e.g., 0.1-0.4 mm, or 0.2-0.5 mm. The devices are typically inserted into an artery that has an internal circumference during systole of 6-8 mm. Thus, the intravascular devices described herein are typically configured to contact less than 35 percent of the circumference of the artery at any longitudinal point along the artery, and at any point in the subject's cardiac cycle. Further typically, the intravascular devices described herein are configured to contact more than 0.5 percent of the circumference of the artery at any longitudinal point along the artery, and at any point in the subject's cardiac cycle. For some applications, the contact region may be 0.5-35 percent of the circumference of the artery.

For some applications, the intravascular devices described herein have a total cross-sectional area of less than 5 sq mm, e.g., less than 0.8 sq mm, or less than 0.5 sq mm. (The total cross-sectional area should be understood to refer to the cross-sectional area of the solid portions of the devices, and not the space in between the solid portions.) The devices typically have this cross-sectional area over a length of the device of more than 4 mm, e.g., more than 6 mm, and/or less than 12 mm, e.g. less than 10 mm. For example, the devices may have the aforementioned cross sectional area over a length of 4 mm-12 mm, e.g., 6 mm-10 mm. The devices are typically manufactured from nitinol, and/or passivated stainless steel 316L.

Figure 9A:
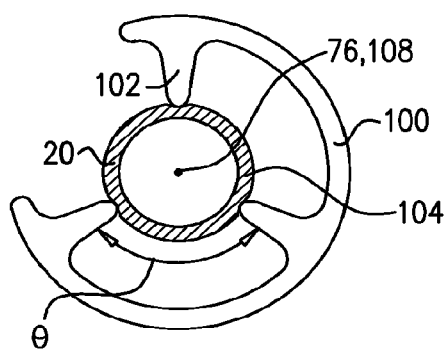

Reference is now made to FIGS. 9A-D, which are schematic illustrations of extravascular devices 100 that are implanted around the outside of artery 20, in accordance with some applications of the present invention. For some applications, an extravascular device having three contact elements 102 (as shown in FIGS. 9A and 9C) is placed around the artery. Alternatively, the extravascular device has a different number of contact elements 102, e.g., four to six contact elements. The contact elements increase the strain in the arterial wall at the regions at which the contact elements contact the arterial wall, relative to the strain in the arterial wall in the absence of device 100. For some applications, the device increases the strain in the arterial wall even at regions of the arterial wall between the contact regions, relative to the strain of the arterial wall in the absence of the device.

As with the intravascular devices described hereinabove, typically contact between extravascular device 100 and the artery at a given longitudinal location is limited to several (e.g., three to six) contact regions around the circumference of the artery, and is generally minimized. Thus, when the device is placed around the artery there is at least one, and typically a plurality of, non-contact regions 104 around the circumference of the artery, at which the device does not contact the arterial wall. As shown in FIG. 9A, each contiguous non-contact region at a given longitudinal site of the artery, encompasses an angle theta around a longitudinal axis 76 of the artery. For some devices, as shown, the angle theta is also defined by the edges of adjacent contact elements 102 of the device and longitudinal axis 108 of the device. When the device is placed in the artery longitudinal axis 108 of the device is typically aligned with longitudinal axis 76 of the artery.

Typically, angle theta is greater than 10 degree, e.g., greater than 20 degree, or greater than 50 degrees. Further typically, angle theta is less than 180 degrees, e.g., less than 90 degrees. For some applications angle theta is 10-180 degree, e.g., 20-90 degrees. This may be beneficial, since providing contiguous non-contact regions around the artery, as described, allows a greater area of the artery to pulsate in response to pressure changes than if the device were to provide smaller contiguous non-contact regions.

FIG. 9B shows a cross-section of one of contact elements 102 on a wall of artery 20, in accordance with some applications of the present invention. For some applications, some or all of contact elements 102 are shaped to define grooves. Each of the grooves has a length L. Typically, length L is more than 0.5 mm (e.g., more than 2 mm), and/or less than 8 mm (e.g., less than 6 mm). For example, length L may be 0.5-8 mm, e.g., 2-6 mm. The contact element typically facilitates pulsation of the arterial wall into the groove.

Typically (as shown for example in FIGS. 9A and 9C), extravascular device 100 does not encompass the full circumference of the artery. For example, the extravascular device may encompass less than 90 percent, e.g., less than 70 percent of the circumference of the artery. For some applications, using a device that does not encompass the whole circumference of the artery facilitates placement of the device on the artery. For example, it may be possible to place such a device on the artery (a) without dissecting the artery free from its surrounding tissues, and/or (b) without fully mobilizing the artery.

For some applications, using a device that does not encompass the whole circumference of the artery reduces damage to the artery, and/or damage to baroreceptors, during placement of the device on the artery. Alternatively or additionally, using a device that does not encompass the whole circumference of the artery makes placement of the device on the artery a less complex procedure than placement on the artery of a device that fully encompasses the artery.

For some applications, device 100 does not encompass the whole circumference of the artery, and contact elements 102 curve around the artery, as shown in FIG. 9C. Typically, the curvature of the contact elements facilitates coupling of device 100 to the artery.

Typically, extravascular device 100 encompasses more than 50 percent of the circumference of the artery, for example, in order to prevent the device from slipping from the artery. However, the scope of the present invention includes devices that encompass less than 50 percent of the artery.

For some applications, extravascular device 100 encompasses the whole circumference of artery 20. For example, an extravascular device may be used that comprises two pieces that are coupled to each other such that the device encompasses the whole artery.

Typically, the device causes an increase in the strain in at least a portion of the arterial wall, relative to the strain in the arterial wall in the absence of the device, without substantially reducing the cross-sectional area of the artery. For example, the cross-sectional area of the artery in the presence of device 100 may be more than 50 percent, e.g., more than 80 percent of the cross-sectional area of the artery in the absence of the device, at a given stage in the subject's cardiac cycle. The device does not cause a substantial reduction in the cross-sectional area of the artery because the device only contacts the artery at discrete points around the circumference of the artery. Therefore the device does not substantially constrict the artery, but rather reshapes the artery relative to the shape of the artery in the absence of the device.

Further typically, the device causes an increase in the strain in at least a portion of the arterial wall, relative to the strain in the arterial wall in the absence of the device, without substantially affecting blood flow through the artery. For example, the rate of blood flow through the artery in the presence of device 100 may be more than 70 percent, e.g., more than 90 percent of the blood flow in the absence of the device.

For some applications, an insubstantial effect on flow is achieved by maintaining an internal diameter of the artery, in the presence of the device, that is at least 30 percent of the diameter of the artery, in the absence of the device, throughout the cardiac cycle. Alternatively or additionally, an insubstantial effect on flow is achieved by maintaining the cross sectional area of the artery, in the presence of the device, to be at least 20 percent of the sectional area, in the absence of the device, at a given stage in the subject's cardiac cycle.

For some applications, the flow through the artery to which the device is coupled is monitored during the implantation of the device, and the device is configured to not reduce the flow by more than 15 percent. For some applications, the degree of force applied to the artery, and/or a physical distance between parts of the device, is modulated until the measured flow is not reduced by more than 15 percent. For some applications the absolute minimal distance across the artery is limited to no less than 1.5 mm.

For some applications, the extravascular devices contact the artery around which they are placed along a length of 5 mm.

For some applications, an extravascular device is used that is in accordance with one or more of the devices described in U.S. patent application Ser. No. 12/602,787 to Gross, which is incorporated herein by reference.

For some applications, a plurality of extravascular devices 100 are placed around the artery, as shown in FIG. 9D. For some applications, the plurality of extravascular devices are coupled to each other by a coupling element 105. The extravascular devices are typically spaced from each other such that there are non-contact regions 103 between each of the extravascular devices. Each of the non-contact regions is contiguous and, typically, has a length L1 of more than 0.5 mm (e.g., more than 2 mm), and/or less than 8 mm (e.g., less than 6 mm). For example, length L1 may be 0.5-8 mm, e.g., 2-6 mm. The arterial wall is typically able to pulsate at the non-contact regions.

Figure 10:
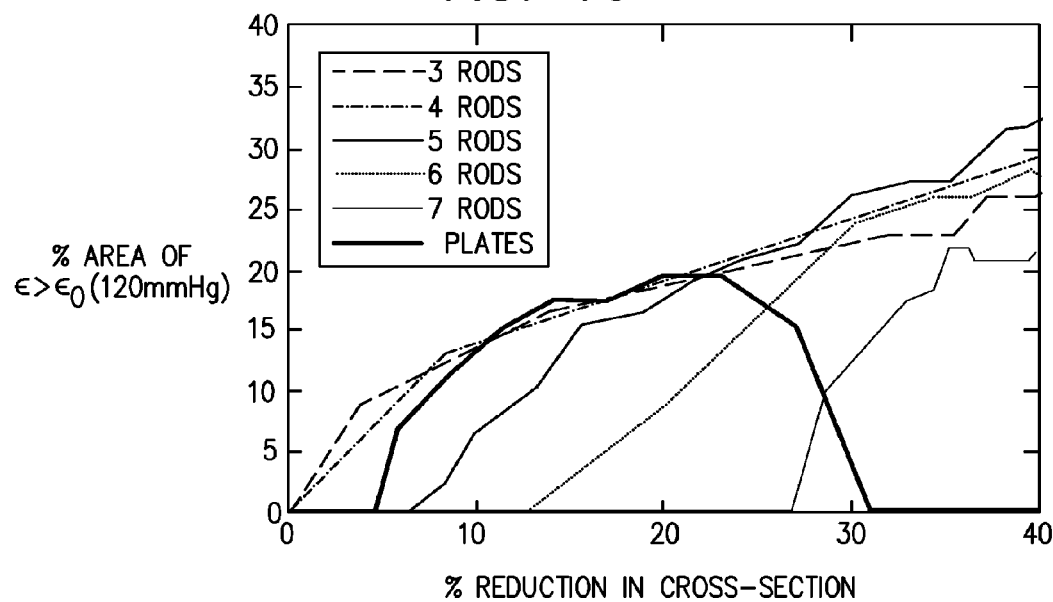
FIG. 10 is a graph that indicates the portion of an arterial wall having a strain that is greater than a threshold value, as a function of the reduction in the cross-sectional area of the artery, for respective extravascular devices, in accordance with some applications of the present invention.

Reference is now made to FIG. 10, which is a graph generated by computer simulation, which indicates the circumferential portion of an arterial wall having a strain that is greater than a threshold value, as a function of the reduction in the cross-sectional area of the artery, for respective extravascular devices. For some applications of the present invention, an extravascular device is placed around an artery, as described hereinabove. Typically, the extravascular device increases strain in at least regions of the arterial wall without substantially reducing the cross-sectional area of the artery, as described hereinabove. Further typically, the extravascular device increases strain in at least regions of the arterial wall without substantially affecting blood flow through the artery, as described hereinabove.

The graph shows several lines, the lines corresponding to extravascular devices that are similar to the extravascular device described hereinabove with reference to FIGS. 3 and 9A. The lines correspond to extravascular devices that have, respectively, three, four, five, six, and seven contact regions with the arterial wall around the circumference of the artery. In addition, one of the lines corresponds to two flat plates that are placed against the outer surface of the artery.

The simulation was generated for an artery at 100 mmHg of pressure. When the extravascular devices herein are placed on the arterial wall, the strain in at least some portions of the arterial wall is increased. Placing the extravascular devices on the arterial wall typically reduces the cross-sectional area of the artery. For a given device, the more the device compresses the artery, the greater the increase in the strain in the arterial walls, and the greater the reduction in the cross-sectional area of the artery.

The x-axis of the graph of FIG. 10 indicates the reduction in the cross-sectional area of the artery generated by the devices. The y-axis measures the percentage of the circumference of the arterial wall having a strain that is at least equivalent to what the strain of the arterial wall would be, if the pressure in the artery were 120 mmHg. Typically, the baroreceptor firing rate in such areas when the pressure is 100 mmHg, during use of the devices described hereinabove, will be generally equivalent to, or greater than the baroreceptor firing rate at 120 mmHg pressure in the absence of use of the devices. Thus, each of the lines in the graph is a measure of the percentage of the circumference of the arterial wall having the increased strain as a function of the reduction in the arterial cross-sectional area that is necessary to induce the increase in strain.

It may be observed that the devices having a smaller number of contact regions with the artery are typically more effective at increasing the strain in the arterial wall by applying a compression force that does not substantially reduce the cross-sectional area of the artery. For example, devices having three and four contact regions with the artery increase the strain of, respectively, 13 percent and 14 percent of the arterial wall to the equivalent of 120 mmHg of pressure while only reducing the cross-sectional area of the artery by 10 percent. Typically, a 10 percent reduction in the cross-sectional area of the artery does not substantially reduce blood flow through the artery in a manner that has significant adverse physiological effects.

The inventors hypothesize that the devices having a larger number of contact regions with the artery are less effective at increasing the strain in the arterial wall than those with a smaller number of contact regions, because the device acts to support the arterial wall at the contact regions, thereby reducing pulsation of the arterial wall over the course of the cardiac cycle. For this reason, the inventors hypothesize that, at low pressures, the two plates are relatively effective at increasing the strain in the arterial wall, since there is a small amount of contact between the plates and the wall. However, at higher compressive forces, the plates provide more support to the wall since there is a greater contact area between the plates and the wall. Therefore, the plates limit the pulsation of the wall by an increasing amount. At higher compressive forces, the decrease in baroreceptor stimulation due to the reduced pulsation of the artery overrides the increase in baroreceptor stimulation due to the plates exerting pressure on the arterial wall. Thus, at higher compressive forces, the plates are not as effective as the other extravascular devices at increasing the strain in regions of the arterial wall. Nevertheless, the scope of the present invention include the use of such plates, e.g., when strain increase is not the only parameter of importance in selecting an implant.

It is additionally noted that for a broad range of allowed reductions in cross-section, e.g., about 17-30 percent, 3-6 contact regions all function generally well. Thus, at higher compression forces (i.e., by reducing the cross-sectional area of the artery by a greater amount), the devices having a greater number of contact regions with the artery become more effective at increasing the strain in the arterial wall. For example, by reducing the cross-sectional area of the artery by 30 percent, each of the devices having three to six contact regions with the artery increases the strain of between 22 percent and 26 percent of the arterial wall to the equivalent of 120 mmHg of pressure.

Figure 11:
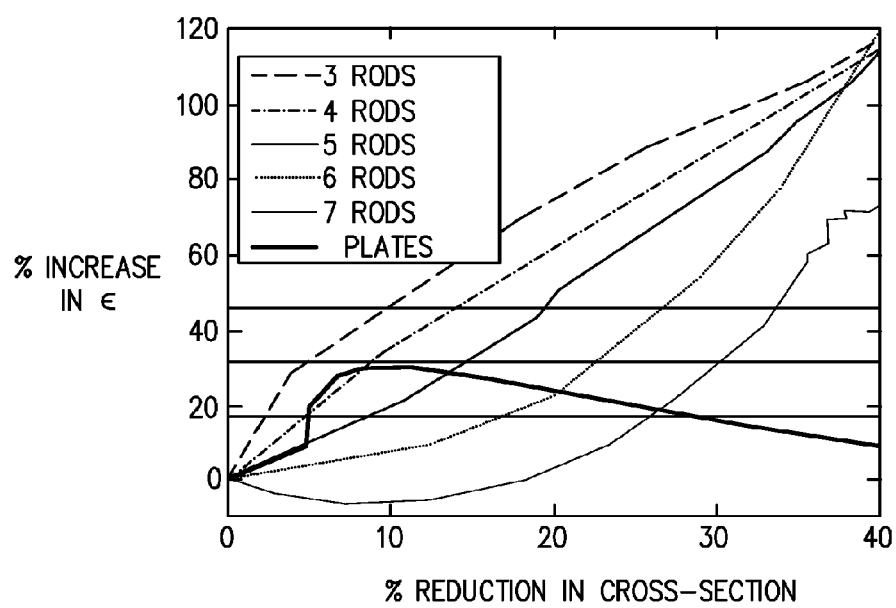
FIG. 11 is a graph showing the maximum percentage increase in the strain of the arterial wall as a function of the reduction in the cross-sectional area of the artery, for respective extravascular devices, in accordance with some applications of the present invention.

Reference is now made to FIG. 11, which is a graph showing the maximum percentage increase in the strain of the arterial wall as a function of the reduction in the cross-sectional area of the artery, for respective extravascular devices.

The graph shows several lines, the lines corresponding to extravascular devices that are similar to the extravascular device described hereinabove with reference to FIGS. 3 and 9A. The lines correspond to extravascular devices that have, respectively, three, four, five, six, and seven contact regions with the arterial wall around the circumference of the artery. In addition, one of the lines corresponds to two plates that are placed against the outside surface of the artery.

The simulation was generated for an artery at 100 mmHg of pressure. The bottom, middle, and top horizontal lines correspond, respectively, to the maximum strain in the vessel wall at 120 mmHg, 140 mmHg, and 160 mmHg pressure, when no device is placed on the artery. When the devices herein are placed on the arterial wall, the maximum strain of the arterial wall is increased. Placing the devices on the arterial wall typically reduces the cross-sectional area of the artery. For a given device, the more the device compresses the artery, the greater the maximum strain in the arterial walls, and the greater the reduction in the cross-sectional area of the artery.

The x-axis of the graph of FIG. 11 measures the reduction in the cross-sectional area of the artery generated by the devices. The y-axis measures the maximum strain in the arterial wall.

It may be observed that for the devices for which the data shown in the graph was generated, the fewer the number of contact regions that the device made with the arterial wall, the more effective the device is at increasing the maximum strain in the arterial wall for a given reduction in the cross-sectional area of the artery that is caused by the device. For example, by compressing the artery such that it has a 20 percent reduction in its cross-sectional area:

the device having three contact regions generates a maximum increase of 75 percent in the arterial wall strain, the device having four contact regions generates a maximum increase of 62 percent in the arterial wall strain, the device having five contact regions generates a maximum increase of 50 percent in the arterial wall strain, the device having six contact regions generates a maximum increase of 23 percent in the arterial wall strain, and the device having seven contact regions generates a maximum increase of less than 5 percent in the arterial wall strain.

Thus, in accordance with some applications of the present invention, extravascular devices having three or more contact regions (e.g., three to six) with the artery are placed around the outside of the artery. The devices typically provide contact regions and non-contact regions of the arterial wall, as described hereinabove. The devices typically increase the strain in the arterial wall, thereby generating increased baroreceptor firing in the artery.

Figure 12:
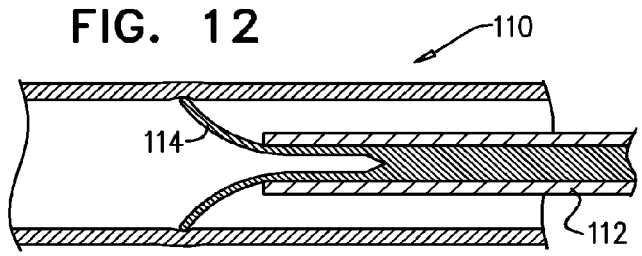
FIG. 12 is a schematic illustration of a device for measuring the baroreceptor response of a subject to pressure that is exerted on the inner wall of an artery of the subject, in accordance with some applications of the present invention.

Reference is now made to FIG. 12, which is a schematic illustration of a device 110 that is used to test the baroreceptor response of a subject to a range of intravascular pressures, in accordance with some applications of the present invention. For some applications, before an intravascular device is inserted into a subject's artery, the baroreceptor response of the subject is tested using measuring device 110. Catheter 112 is inserted into artery 20, in which the intravascular device will be implanted. Extendable arms 114 are extendable from the distal end of the catheter, and are configured such that the pressure that the arms exert on the arterial wall increases, as the portion of the arms that extends from the catheter increases.

Extendable arms 114 are extended incrementally from the distal end of the catheter. At each of the increments, the subject's blood pressure is measured in order to determine the baroreceptor response to the pressure that the arms are exerting on the arterial wall. On the basis of the blood pressure measurements, it is determined which intravascular device should be inserted into the subject's artery, and/or what dimensions the intravascular device should have.

For some applications, a measuring device including arms 114 or a similar measuring device is left in place in the artery, but catheter 112 is removed before the blood pressure measurements are taken. For example, the catheter may be removed in order to increase blood flow through the artery, relative to when the catheter is in place. Once it has been determined, using the measuring device, which intravascular device should be placed inside the artery, and/or what dimensions the intravascular device should have, the measuring device is removed from the artery and the intravascular device is placed inside the artery.

For some applications, a toroid balloon is placed inside the artery and is used as a measuring device. The balloon is inflated incrementally such that the balloon applies varying amounts of pressure to the arterial wall, and the subject's blood pressure is measured in order to measure the response to the pressure being applied to the wall. In this manner, it is determined which intravascular device should be used, and/or what dimensions the intravascular device should have. During the aforementioned measuring procedure, blood continues to flow through the artery, via a central hole in the toroid balloon.

For some applications, the intravascular devices described herein are inserted to an implantation site inside or (using a non-transvascular route) outside of the subject's artery, while the device is in a first configuration thereof. When the device has been placed at the implantation site, the configuration of the device is changed to a second configuration, in which the device is effective to increase baroreceptor stimulation, in accordance with the techniques described herein. For example, the device may be made of nitinol, or another shape memory material, and the configuration of the device may be changed by applying an RF signal to the device. For some applications, the device is implanted at an implantation site that is close to the subject's skin, and the RF signal is applied to the device via the subject's skin.

For some applications, devices are applied to the carotid artery of a subject who suffers from carotid sinus hypersensitivity, in order to reduce baroreceptor sensitivity of the carotid sinus, by reducing pulsation of the artery. For example, a device may be placed inside or outside the artery such that the device makes contact with the artery at more than six contact points, and/or over more than 180 degrees of the circumference of the artery. For some applications, a device (e.g., a stent) is placed inside or outside of the artery such that the device makes 270-360 degrees of contact with the artery.

Figure 13:
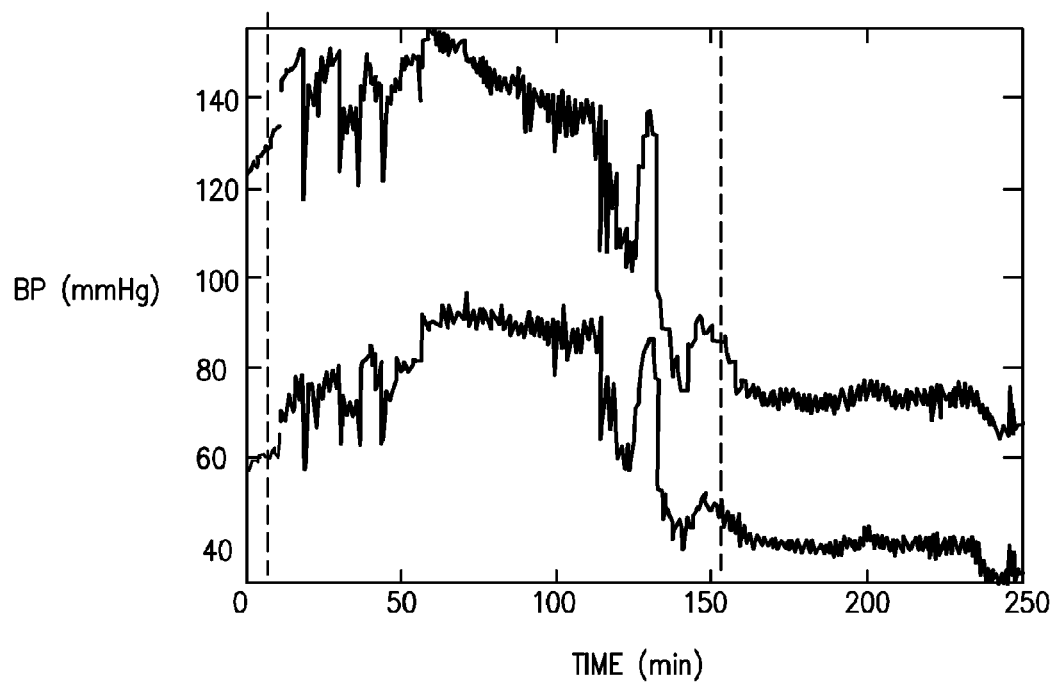
FIG. 13 is a graph showing the blood pressure measured in a dog before and after the insertion of intravascular devices into the dog's carotid sinuses, in accordance with some applications of the present invention.

Reference is now made to FIG. 13, which is a graph showing blood pressure measured in a dog, before, during and after the bilateral placement of intravascular devices into the dog's carotid sinuses, in accordance with some applications of the present invention. Intravascular devices which made contact with the carotid sinus at four contact regions (the devices being generally as shown in FIGS. 7A-B) were placed in the dog's left and right carotid sinuses. The beginning and end of the implantation period is indicated in FIG. 13 by, respectively, the left and right vertical dashed lines at about five minutes and 153 minutes.

It may be observed that the implantation of the devices in both sinuses resulted in the dog's systolic blood pressure dropping from above 120 mmHg to below 80 mmHg, and in the dog's diastolic blood pressure dropping from about 60 mmHg to about 40 mmHg. During the implantation procedure the dog's blood pressure rose. The inventors hypothesize that the rise in blood pressure is due to catheters blocking the flow of blood to the carotid arteries during the implantation, resulting in reduced baroreceptor stimulation during the implantation procedure.

Figure 14:
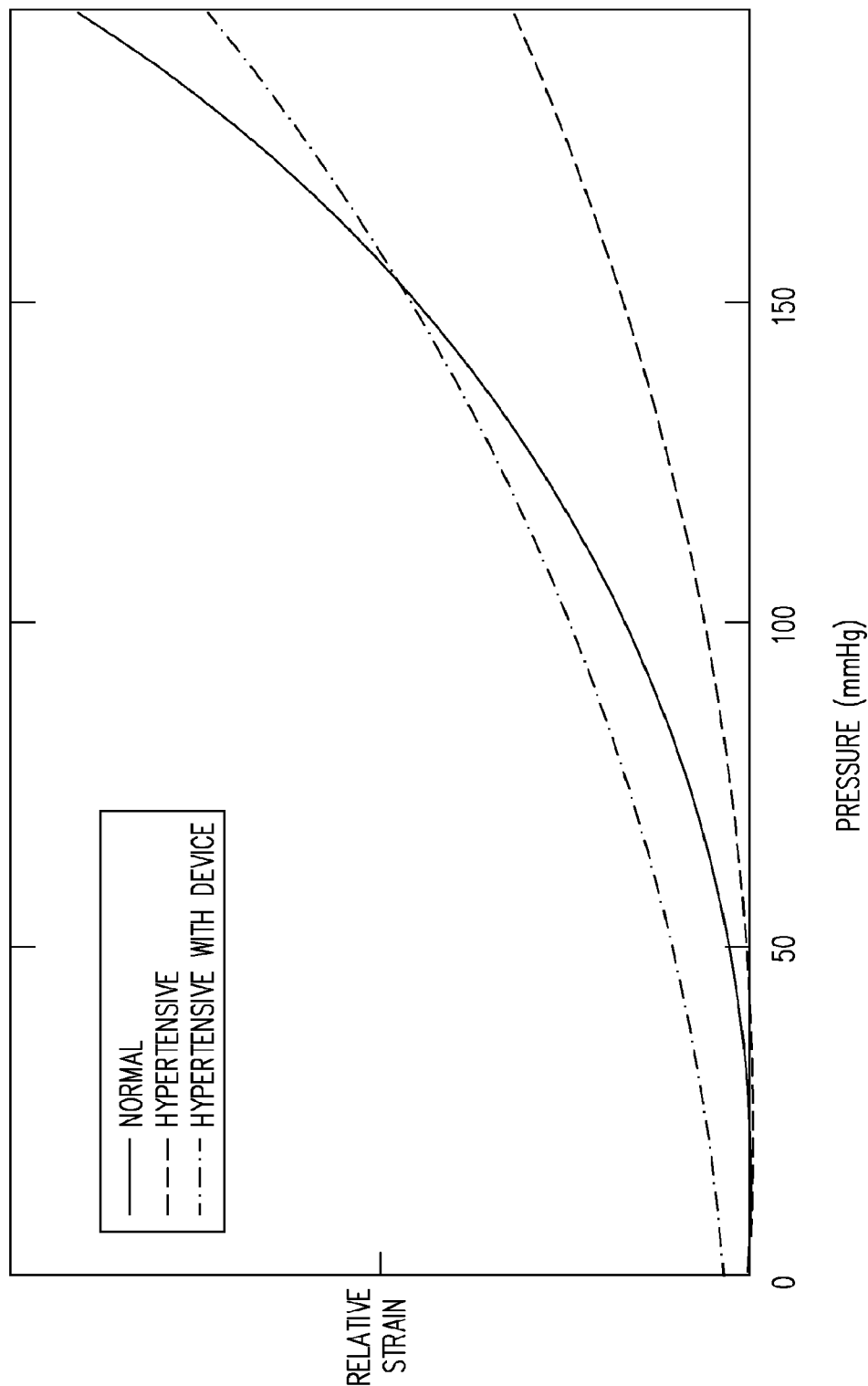
FIG. 14 is a graph showing the pressure-strain curve of the artery of a healthy subject, a hypertensive subject, and a hypertensive subject that uses a device as described herein, in accordance with some applications of the present invention.

Reference is now made to FIG. 14, which is a graph showing the pressure-strain curve of an artery of a normal subject, a hypertensive subject, and a hypertensive subject who uses one of the devices described herein. One of the causes of hypertension is that the arterial wall of the subject does not experience as much strain at any given pressure, as the arterial wall of a normal subject. Thus, the pressure-strain curve of the hypertensive subject is flattened with respect to that of a healthy subject and the strain response is shifted to higher pressures.

The devices described herein increase the strain in the arterial wall at all pressure levels within the artery. For some applications, as shown, at increasing arterial pressures, the absolute increase in the strain in the arterial wall caused by the device increases, relative to the strain experienced by the hypertensive subject before implantation of the device. Thus, the devices described herein both shift the pressure-strain curve of a hypertensive subject upwards and increase the gradient of the curve. A device is typically selected such that the subject's pressure-strain curve, subsequent to implantation of the device, will intersect the normal pressure-strain curve at a pressure of between 80 mmHg and 240 mmHg.

The scope of the present invention includes combining the apparatus and methods described herein with those described in US 2008/0033501 to Gross, and/or US Patent application Ser. No. 12/602,787 to Gross, both of which applications are incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method of stimulating baroreceptors to treat a disease of a patient, the patient having a carotid artery with a wall, the method comprising:
   providing an implant having a first structure on a first end and a second structure on a second end opposite the first end, wherein three to five longitudinal contact regions extend in a longitudinal direction between the first end and the second end; and
   placing the implant in the carotid artery with an expanded configuration, wherein the three to five longitudinal contact regions contact the wall of the carotid artery and define three to five contact regions of the wall alternating with three to five flat non-contact regions around the wall, wherein the three to five contact regions of the wall alternating with the three to five flat non-contact regions stretch the wall of the carotid artery sufficiently to stimulate the baroreceptors and treat the disease.

2. The method of claim 1, wherein the three to five contact regions of the wall alternating with the three to five flat non-contact regions around the wall shape the wall to a polygonal cross-sectional shape having from three to five sides.

3. The method of claim 1, wherein the three to five longitudinal contact regions are spaced apart with distances sized to increase a cross-section of the carotid artery and flatten the non-contact regions in order to lower blood pressure.

4. The method of claim 1, wherein the three to five contact regions of the wall alternating with the three to five flat non-contact regions around the wall shift a pressure-strain curve of a hypertensive patient upwards and increase a gradient of the pressure-strain curve.

5. The method of claim 1, wherein the three to five longitudinal contact regions comprise from three to five longitudinal contact regions and shape a cross-section of the wall to a polygonal shape having from three to five sides.

6. The method of claim 1, wherein the three to five longitudinal contact regions comprise four longitudinal contact regions spaced apart to shape the wall to a cross-sectional shape having four flat sides.

7. A method as in claim 1 further comprising:
   identifying a subject as suffering from hypertension; and
   in response to the identifying, placing the implant in the carotid artery, wherein the three to five flat non-contact regions around the wall pulsate and stimulate the baroreceptors to treat the hypertension.

* * * * *